United States Patent
Nazeeruddin et al.

(10) Patent No.: US 8,039,124 B2
(45) Date of Patent: Oct. 18, 2011

(54) ELECTRO LUMINESCENT METAL COMPLEXES

(75) Inventors: Mohammad Khaja Nazeeruddin, Ecublens (CH); Rene Theodorus Wegh, Eindhoven (NL); Steve Klink, Eindhoven (NL); Michael Graetzel, St. Sulpice (CH); Cedric Nicolas Klein, Lausanne (CH)

(73) Assignee: Koninklijke Philips Electronics N.V., Eindhoven (NL)

( * ) Notice: Subject to any disclaimer, the term of this patent is extended or adjusted under 35 U.S.C. 154(b) by 925 days.

(21) Appl. No.: 11/993,483

(22) PCT Filed: Jun. 26, 2006

(86) PCT No.: PCT/IB2006/052092
§ 371 (c)(1),
(2), (4) Date: Dec. 21, 2007

(87) PCT Pub. No.: WO2007/004113
PCT Pub. Date: Jan. 11, 2007

(65) Prior Publication Data
US 2010/0044637 A1  Feb. 25, 2010

(30) Foreign Application Priority Data
Jun. 30, 2005 (EP) .................... 05105935

(51) Int. Cl.
*H01L 51/54* (2006.01)
*C09K 11/06* (2006.01)

(52) U.S. Cl. ........ 428/690; 428/917; 313/504; 313/506; 252/301.16; 257/40; 257/E51.044; 546/4

(58) Field of Classification Search .................. None
See application file for complete search history.

(56) References Cited

U.S. PATENT DOCUMENTS

| | | | |
|---|---|---|---|
| 6,815,091 B2 * | 11/2004 | Takiguchi et al. | 428/690 |
| 2002/0182441 A1 * | 12/2002 | Lamansky et al. | 428/690 |
| 2003/0059646 A1 * | 3/2003 | Kamatani et al. | 428/690 |
| 2004/0086742 A1 * | 5/2004 | Ma et al. | 428/690 |
| 2004/0121184 A1 * | 6/2004 | Thompson et al. | 428/690 |
| 2005/0031904 A1 | 2/2005 | Igarashi et al. | |
| 2005/0037233 A1 | 2/2005 | Dobbs et al. | |
| 2005/0048312 A1 | 3/2005 | Herron et al. | |
| 2005/0164029 A1 * | 7/2005 | Burn et al. | 428/690 |

FOREIGN PATENT DOCUMENTS

| | | |
|---|---|---|
| EP | 0 074 807 A1 * | 3/1983 |
| WO | 2004043974 A1 | 5/2004 |
| WO | 2006011090 A1 | 2/2006 |

OTHER PUBLICATIONS

Xiaodong Wang, et: Novel Iridium Complex and its Copolymer with N-Vinyl Carbazole for Electroluminescent Devices, IEEE Journal of Selected Topics in Quantum Electronics vol. 10, No. 1, Jan./Feb. 2004, pp. 121-126.

Michael S. Lowry, et al: Accelerated Luminophore Discovery Through Combinatorial Synthesis, vol. 126, No. 43, Nov. 3, 2004, pp. 14129-14135, XP009057980.

Nazeeruddin, et al: Highly Phosphorescence Iridium Complexes and Their Application in Organic Light-Emitting Devices, vol. 125, No. 29, Jul. 23, 2003, pp. 8790-8797, XP009057719.

Lok-Hei Lui, et al: New Luminescent Cyclometalated Iridium III Diimine Complexes as Biological Labeling Reagents, Inorganic Chemistry, vol. 42, No. 21, Sep. 17, 2003, pp. 6886-6897, XP00234215.

Fernandez-Sanchez, et al: Novel Nanostructured Materials to Develop Oxygen-Sensitive Films for Optical Sensors Analytica Chemica Acta, vol. 566, No. 2, May Apr. 2006, pp. 271-282, XP005407875.

* cited by examiner

*Primary Examiner* — Callie Shosho
*Assistant Examiner* — Michael H Wilson
(74) *Attorney, Agent, or Firm* — David Zivan; Mark L. Beloborodov

(57) ABSTRACT

Electro luminescent metal, e.g. Ir, complexes are disclosed. The metal complexes comprise at least one ligand L1 and at least one ligand L2, wherein ligand L1 is a 2-phenylpyridine ligand (I), comprising a phenyl ring (A) and a pyridine ring (B). The integers 2 to 9 denote positions in which substitutions can be made, and by the use of different substituents, e.g. 2,4-difluoro and 7-N(CH3)2, the emission wavelength of the complex may be tuned. The ligand L2 may e.g. be a compound of the following formula (II).

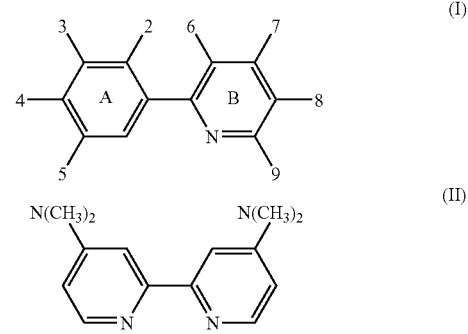

12 Claims, 12 Drawing Sheets

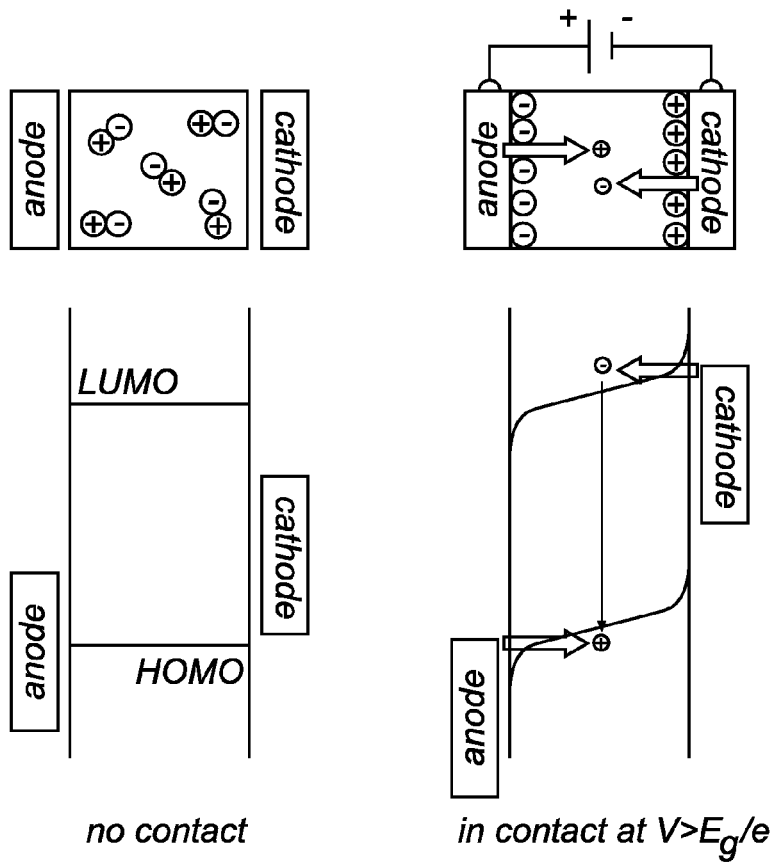
*Fig. 1a*  *Fig. 1b*
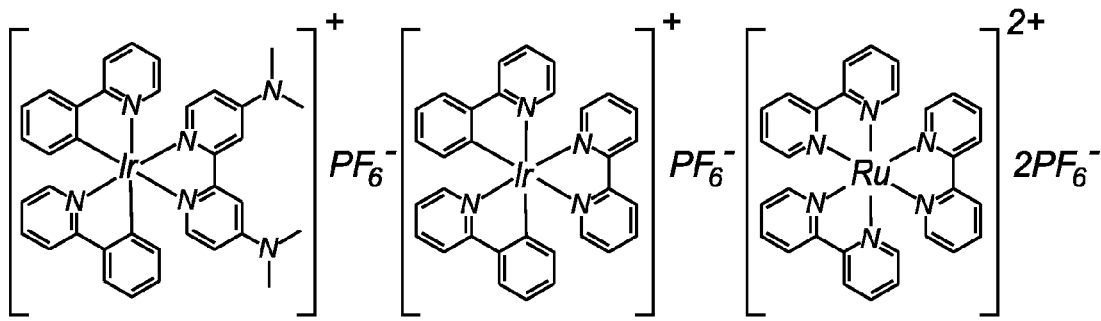
*Fig. 2a*  *Fig. 2b*  *Fig. 2c*

ELECTRO LUMINESCENT METAL COMPLEXES

FIELD OF THE INVENTION

The present invention relates to metal complexes, and the use of such complexes as an electro luminescent material. It also relates to a light-emitting device comprising such metal complexes, and to a method for manufacturing such a light-emitting device.

BACKGROUND OF THE INVENTION

Organic electronic devices that emit light, such as light-emitting diodes that make up displays, are present in many different kinds of electronic equipment. In all such devices, an organic active layer is sandwiched between two electrical contact layers. At least one of the electrical contact layers is light transmitting so that light can pass through the electrical contact layer. The organic active layer emits light through the light-transmitting electrical contact layer upon application of a voltage across the electrical contact layers.

Due to rapid progress in the development of organic light-emitting materials, devices based on these materials, called PLEDs and OLEDs (polymer and small-molecule organic light-emitting diodes), are entering the display market.

A very promising alternative to PLED/OLED, particularly for large-area lighting applications, is the light-emitting electrochemical cell (LEEC) [1]. A LEEC does not need a low-workfunction metal electrode and thicker organic active layers can be used, while keeping the operating voltage low. The operating mechanism is based on the presence of mobile ions.

FIG. 1 schematically shows the operating mechanism of a LEEC; the top pictures are cross sections, and the bottom pictures are energy band diagrams. (a) shows the relative positions of the energy levels when the layers are not in contact: the Fermi levels of the electrodes are not matched with the HOMO and LUMO levels of the electro luminescent layer. The ions in that layer reside in pairs. (b) shows the situation when a voltage is applied high enough to overcome the band gap of the electro luminescent layer: the ions have moved to opposite electrodes so that strong voltage drops are created, making charge carrier injection and thus electro luminescence possible.

Thus, upon application of a voltage, the cations and anions move towards the cathode and anode respectively, leading to large electric fields at the electrode interfaces. The ion distribution formed facilitates injection of electrons and holes at the cathode and the anode respectively, thus allowing transport and recombination of the charge carriers, which results in emission of a photon.

For lighting applications the generation of white light is essential. In case of organic light emitting devices, this can be obtained by e.g. combining blue and orange/yellow emission or blue, green and red emission. The orange/yellow, green and red emission can be obtained by electro luminescence, or by photoluminescence upon absorbing part of the emitted blue light. In all cases, the generation of blue light by electro luminescence is necessary.

The highest efficiencies of light generation are achieved by using triplet emitters, in particular Ir-complexes. These can be made to emit light of any colour by proper substitution of the ligands and proper charge of the complex. For instance, $[Ir(ppy)_2(bpy)]^+(PF_6^-)$ emits yellow light.

The photophysical and photochemical properties of $d^6$ metal complexes such as ruthenium (II), osmium (II), rhenium (I), rhodium (III) and iridium (III) have been thoroughly investigated during the last two decades. The fundamental thrust behind these studies is to understand the energy and electron transfer processes in the excited state and to apply this knowledge to potential practical applications, such as solar energy conversion, organic light-emitting diodes, electro luminescence and in sensors. The main requirements for organic light-emitting devices are that the complexes should exhibit very high phosphorescence quantum efficiencies and sharp emission spectra in the visible region, preferably with the maxima around 440 nm (blue), 530 nm (green) and 640 nm (red). This is of importance for display (wide colour gamut) as well as lighting (high colour rendering index) applications. Several groups have used extensively iridium (III) based complexes in light-emitting devices and obtained up to 12.3% external quantum efficiencies [5].

The origin of emission in iridium complexes containing the 2-phenylpyridine ligand is the charge transfer excited states decay through radiative pathways, which are known to exhibit high quantum yields due to mixing the singlet and the triplet excited states via spin-orbit coupling. Nevertheless, the majority of charged iridium (III) complexes known to date largely remained as green or yellow emitters and pure blue and red emitting complexes are scarce [6].

Blue electro luminescence has been obtained by fluorine substitution of the ligands of Ir complexes [2], [3], [4]. Fluorine substitution is also described in US 2005/0037233. One disadvantage is that all fluorine-substituted blue-emitting Ir complexes known are neutral, which is a disadvantage for LEECs. The metal complex emitters for LEECs should preferably be charged since then they also provide the ions needed to enable charge injection. Also for neutral Ir complexes it remains a challenge to shift the emission spectrum further into the blue and red. Further, for lighting applications, it may be advantageous to be able to tune the emission wavelength to other colours, e.g. yellow or orange as described above. Thus, there is a continuing need for electro luminescent compounds.

SUMMARY OF THE INVENTION

To overcome the above-mentioned problems, the present inventors have designed metal complexes having at least one 2-phenylpyridine ligand, in which donor groups, such as dimethylamino, are introduced on the pyridine ring to increase the LUMO level of the complex ($\pi^*$ orbitals of the ligand), and/or acceptor groups, such as 2,4-difluoro, are introduced on the phenyl ring to decrease the HOMO level. By varying the ligands and substituents suitably, the emission spectrum can be tuned to any visible wavelength.

Thus, the present invention relates to electro luminescent metal, e.g. Ir, complexes. The metal complexes comprise at least one ligand L1 and at least one ligand L2, wherein ligand L1 is a 2-phenylpyridine ligand (I), comprising a phenyl ring (A) and a pyridine ring (B):

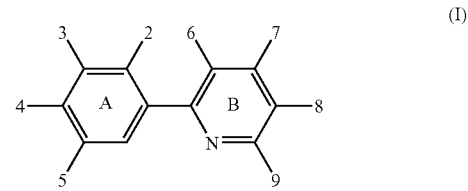

The integers 2 to 9 denote positions in which substitutions can be made, and by the use of different substituents, e.g.

2,4-difluoro and 7-N(CH$_3$)$_2$, the emission wavelength of the complex may be tuned. The ligand L2 may e.g. be a compound of the following formula:

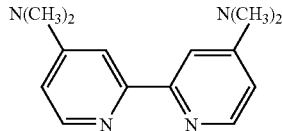

More particularly, the present invention relates to metal complexes having at least one metal atom selected from the group consisting of Ir, Os, Ru, Pd, Pt, Re and Zn, said metal complex comprising at least one ligand L1 and at least one ligand L2, wherein ligand L1 is a 2-phenylpyridine ligand (I), comprising a phenyl ring (A) and a pyridine ring (B),

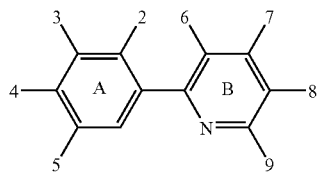

(I)

where the integers 2 to 9 denote positions in which substitutions can be made.

The phenyl ring (A) is non-substituted or substituted in one of the following ways:
position 2=fluoro and position 4=fluoro; or
position 3=fluoro and position 5=fluoro; or
position 3=OR;
R being the same or different at each occurrence and is H, alkyl, aryl, or adjacent R groups can join together to form a 5- or 6-membered ring.

The pyridine ring (B) is non-substituted or substituted in one of the following ways:
position 7=R, CO$_2$R, 4-dimethylaminostyryl, NR$_2$, OR, or a compound of the following formula (II):

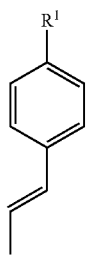

(II)

wherein R$^1$ is H, R, CO$_2$R, OR, 4-dimethylaminostyryl, or NR$_2$; or
position 7=NR$_2$ or OR and position 9=NR$_2$ or OR
R being the same or different at each occurrence and is H, alkyl, aryl, or adjacent R groups can join together to form a 5- or 6-membered ring.
The ligand L2 comprises at least one compound selected from the group consisting of:
a compound of formula (I) as defined above,
a compound of formula CN,
a compound of formula NCS, or
a compound of the following formulas III, IV, or V:

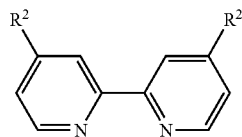

(III)

wherein R$^2$ is selected from NR$_2$ or OR;

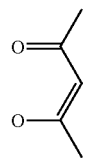

(IV)

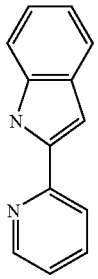

(V)

R being the same or different at each occurrence and is H, alkyl, aryl, or adjacent R groups can join together to form a 5- or 6-membered ring.
The following provisos apply:
when said metal atom is Ir, said phenyl ring (A) is substituted in position 2 and 4 by fluoro, and said pyridyl ring (B) is substituted in position 7 with N(CH$_3$)$_2$, then said ligand L2 is not a compound of formula (IV);
when said metal atom is Ir, said phenyl ring (A) is substituted in position 2 and 4 by fluoro, and said pyridyl ring (B) is substituted in position 7 with N(CH$_3$)$_2$, then said ligand L2 is not a compound of formula (I), wherein said phenyl ring (A) is substituted in position 2 and 4 by fluoro and said pyridyl ring (B) is substituted in position 7 with N(CH$_3$)$_2$.
The metal complex may be neutral, anionic or cationic. Anionic and cationic complexes may comprise (R$^3$)$_4$N$^+$, NH$_4^+$, (R$^3$)$_4$P$^+$, Li$^+$, Na$^+$, K$^+$, Rb$^+$, Cs$^+$, Ag$^+$, Cu$^+$, PF$_6^-$, F$^-$, Cl$^-$, I$^-$, Br$^-$, ClO$_4^-$, BF$_4^-$, CF$_3$SO$_3^-$, (R$^3$)$_4$B$^-$, or mixtures thereof, wherein R$^3$ is an alkyl or aryl group. Suitably, R$^3$ is butyl.
Preferred complexes according to the invention are complexes in which:
said phenyl ring (A) is non-substituted;
said pyridine ring (B) is substituted in position 7 by R; and
ligand L2 comprises two compounds of formula CN, and the metal complex further comprises e.g. Bu$_4$N$^+$ (e.g. complex 1-2 of Example 3 below); or
said phenyl ring (A) is non-substituted;
said pyridine ring (B) is substituted in position 7 by NR$_2$;
ligand L2 comprises two compounds of formula CN, and the metal complex further comprises e.g. Bu$_4$N$^+$ (e.g. complex 1-5 of Example 3 below); or said phenyl ring (A) is substituted by fluoro in position 2 and 4;
said pyridine ring (B) is substituted in position 7 by $NR_2$; and
ligand L2 comprises two compounds of formula CN, and the metal complex further comprises e.g. $Bu_4N^+$ (e.g. complex 1-6 of Example 3 below); or
said phenyl ring (A) is substituted by fluoro in positions 2 and 4;
said pyridine ring (B) is non-substituted; and
ligand L2 comprises two compounds of formula CN and the metal complex further comprises e.g. $Bu_4N^+$ (e.g. complex 1-9 of Example 3 below); or
said phenyl ring (A) is non-substituted;
said pyridine ring (B) is substituted in position 7 by $NR_2$; and
ligand L2 comprises two compounds of formula NCS and the metal complex further comprises e.g. $Bu_4N^+$ (e.g. complex 2-5 of Example 3 below);
said phenyl ring (A) is substituted by fluoro in position 2 and 4;
said pyridine ring (B) is substituted in position 7 by $NR_2$; and
ligand L2 comprises two compounds of formula NCS, and the metal complex further comprises e.g. $Bu_4N^+$ (e.g. complex 2-6 of Example 3 below);
said phenyl ring (A) is substituted by fluoro in position 2 and 4;
said pyridine ring (B) is non-substituted; and
ligand L2 comprises two compounds of formula NCS, and the metal complex further comprises e.g. $Bu_4N^+$ (e.g. complex 2-9 of Example 3 below); or
said phenyl ring (A) is non-substituted; and
said pyridine ring (B) is non-substituted; and
ligand L2 comprises a compound of formula (III), wherein $R^2$ is $NR_2$, and the metal complex further comprises e.g. $PF_6^-$ (e.g. complex 3-1 of Example 3 below); or
said phenyl ring (A) is non-substituted; and
said pyridine ring (B) is substituted by R in position 7; and
ligand L2 comprises a compound of formula (III), wherein $R^2$ is $NR_2$, and the metal complex further comprises e.g. $PF_6^-$ (e.g. complex 3-2 of Example 3 below); or
said phenyl ring (A) is non-substituted; and
said pyridine ring (B) is substituted by $CO_2R$ in position 7; and
ligand L2 comprises a compound of formula (III), wherein $R^2$ is $NR_2$, and the metal complex further comprises e.g. $PF_6^-$ (e.g. complex 3-3 of Example 3 below); or
said phenyl ring (A) is non-substituted; and
said pyridine ring (B) is substituted by 4-dimethylaminostyryl in position 7; and
ligand L2 comprises a compound of formula (III), wherein $R^2$ is $NR_2$, and the metal complex further comprises e.g. $PF_6^-$ (e.g. complex 3-4 of Example 3 below); or
said phenyl ring (A) is substituted by fluoro in positions 2 and 4;
said pyridine ring (B) is substituted in position 7 by $NR_2$; and
ligand L2 comprises a compound of formula (III), wherein $R^2$ is $NR_2$, and the metal complex further comprises e.g. $PF_6^-$ (e.g. complex 3-6 of Example 3 below); or
said phenyl ring (A) is substituted by fluoro in positions 2 and 4;
said pyridine ring (B) is non-substituted; and
ligand L2 comprises a compound of formula (III), wherein $R^2$ is $NR_2$, and the metal complex further comprises e.g. $PF_6^-$ (e.g. complex 3-9 of Example 3 below); or said phenyl ring (A) is non-substituted;
said pyridine ring (B) is non-substituted; and
ligand L2 comprises a compound of formula (III), wherein $R^2$ is OR, and the metal complex further comprises e.g. $PF_6^-$ (e.g. complex 4-1 of Example 3 below); or
said phenyl ring (A) is substituted by fluoro in positions 2 and 4;
said pyridine ring (B) is substituted in position 7 by $NR_2$; and
ligand L2 comprises a compound of formula (III), wherein $R^2$ is OR, and the metal complex further comprises e.g. $PF_6^-$ (e.g. complex 4-6 of Example 3 below); or
said phenyl ring (A) is substituted by fluoro in positions 2 and 4;
said pyridine ring (B) is substituted in position 7 and 9 by $NR_2$; and
ligand L2 comprises two compounds of formula CN, and the metal complex further comprises e.g. $Bu_4N^+$. (e.g. complex 5-1 of Example 3 below);
said phenyl ring (A) is non-substituted;
said pyridine ring (B) is substituted in position 7 by R; and
ligand L2 comprises a compound of formula (IV) (e.g. complex 9-1 of Example 3 below); or
said phenyl ring (A) is non-substituted;
said pyridine ring (B) is substituted in position 7 by $CO_2R$; and
ligand L2 comprises a compound of formula (IV) (e.g. complex 9-2 of Example 3 below); or
said phenyl ring (A) is non-substituted;
said pyridine ring (B) is substituted in position 7 by 4-dimethylaminostyryl; and
ligand L2 comprises a compound of formula (IV) (e.g. complex 9-3 of Example 3 below); or
said phenyl ring (A) is non-substituted;
said pyridine ring (B) is substituted in position 7 by $NR_2$; and
ligand L2 comprises a compound of formula (IV) (e.g. complex 9-4 of Example 3 below); or
said phenyl ring (A) is substituted by fluoro in positions 3 and 5;
said pyridine ring (B) is substituted in position 7 by $NR_2$; and
ligand L2 comprises a compound of formula (IV) (e.g. complex 9-6 of Example 3 below); or
said phenyl ring (A) is substituted by OR in position 3;
said pyridine ring (B) is substituted in position 7 by $NR_2$; and
ligand L2 comprises a compound of formula (IV) (e.g. complex 9-7 of Example 3 below); or
said phenyl ring (A) is non-substituted;
said pyridine ring (B) is substituted in position 7 by $NR_2$; and
ligand L2 comprises a compound of formula (I),
wherein said phenyl ring (A) is non-substituted; and
said pyridine ring (B) is substituted in position 7 by $NR_2$ (e.g. complex 10-4 of Example 3 below); or
said phenyl ring (A) is substituted by fluoro in positions 2 and 4;
said pyridine ring (B) is substituted in position 7 and 9 by $NR_2$; and
ligand L2 comprises a compound of formula (IV) (e.g. complex 11-1 of Example 3 below); or
said phenyl ring (A) is substituted by fluoro in positions 2 and 4;
said pyridine ring (B) is substituted in position 7 and 9 by $NR_2$; and ligand L2 comprises a compound of formula (I),
wherein said phenyl ring (A) is substituted by fluoro in positions 2 and 4; and
said pyridine ring (B) is substituted in position 7 and 9 by $NR_2$ (e.g. complex 12-1 of Example 3 below); or
said phenyl ring (A) is non-substituted;
said pyridine ring (B) is substituted in position 7 by $NR_2$; and
ligand L2 comprises a compound of formula (V) (e.g. complex 13-5 of Example 3 below); or
said phenyl ring (A) is non-substituted;
said pyridine ring (B) is substituted in position 7 by a compound of formula (II), wherein $R^1$ is H; and
ligand L2 comprises a compound of formula (IV) (e.g. complex 14-1 of Example 3 below).

For example, the metal complex according to the invention may comprise two L1 ligands and one or two L2 ligands. Suitably, the metal atom is Ir.

In the case of a non-substituted phenyl ring, it may comprise H in the positions 2, 3, 4 and 5, in the case of a non-substituted pyridine ring, it may comprise H in the positions 6, 7, 8 and 9. However, a non-substituted phenyl ring may comprise any chemical moiety in the positions 2, 3, 4 and 5, and a non-substituted pyridine ring may comprise any chemical moiety in the positions 6, 7, 8 and 9. E.g. the chemical moiety may be an alkyl or aryl group.

In the embodiments outlined above, R is suitably $CH_3$.

A preferred metal complex according to the invention has the following formula:

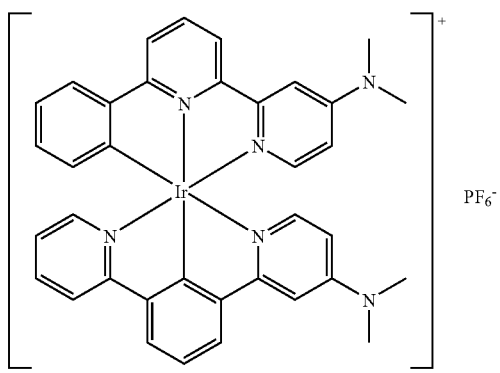

The present invention also relates to the use of such metal complexes as an electro luminescent material. Further, it relates to a light-emitting device comprising such a metal complex. It also relates to a method for manufacturing a light-emitting device comprising arranging an electro luminescent material between at least two electrodes, wherein said electro luminescent material comprises a metal complex according to the invention.

BRIEF DESCRIPTION OF THE DRAWINGS

FIG. 1 schematically shows the operating mechanism of a LEEC.

FIG. 2 shows the molecular structures of the complexes $[Ir(ppy)_2(4,4'-dma-bpy)]^+(PF_6^-)$ (a), $[Ir(ppy)_2(bpy)]^+(PF_6^-)$ (b), and $[Ru(bpy)_3]^{2+}(PF_6^-)_2$ (c).

DETAILED DESCRIPTION OF THE INVENTION

The disclosed concept on metal complexes, in particular iridium (III) complexes, with relevance to their application in OLED and/or LEEC are focused on designing new cyclometalating ligands and/or auxiliary ligands (i.e. ligands which are not cyclometalating) to tune emission spectra of the resulting complexes to any desired emission wavelength by modulating HOMO and LUMO orbitals.

Up to now most strategies for tuning emission spectra of iridium complexes in the blue region have been substitution of acceptor groups on the phenyl ring of 2-phenylpyridine, which stabilizes the HOMO orbitals, i.e. decreases the HOMO energy level of the complex ($t_{2g}$ orbitals of iridium). However, stabilization of the HOMO orbitals also partially stabilizes the LUMO orbitals resulting in less than expected increase of the HOMO-LUMO gap i.e. less blue shift of the emission spectra of the complexes relative to unsubstituted tris 2-phenylpyridine iridium (III) ($Ir(ppy)_3$).

The neutral metal complexes according to the invention exhibit significantly increased separation between the HOMO and LUMO levels compared to $Ir(ppy)_3$ resulting in emission in the blue region. According to the invention, it is also possible to tune the emission properties of neutral complexes into the red region around 650 nm by introducing ligands having notably lower LUMO orbitals (see complexes 9-2, 9-3 and 14 of example 3 below).

Figure 3:
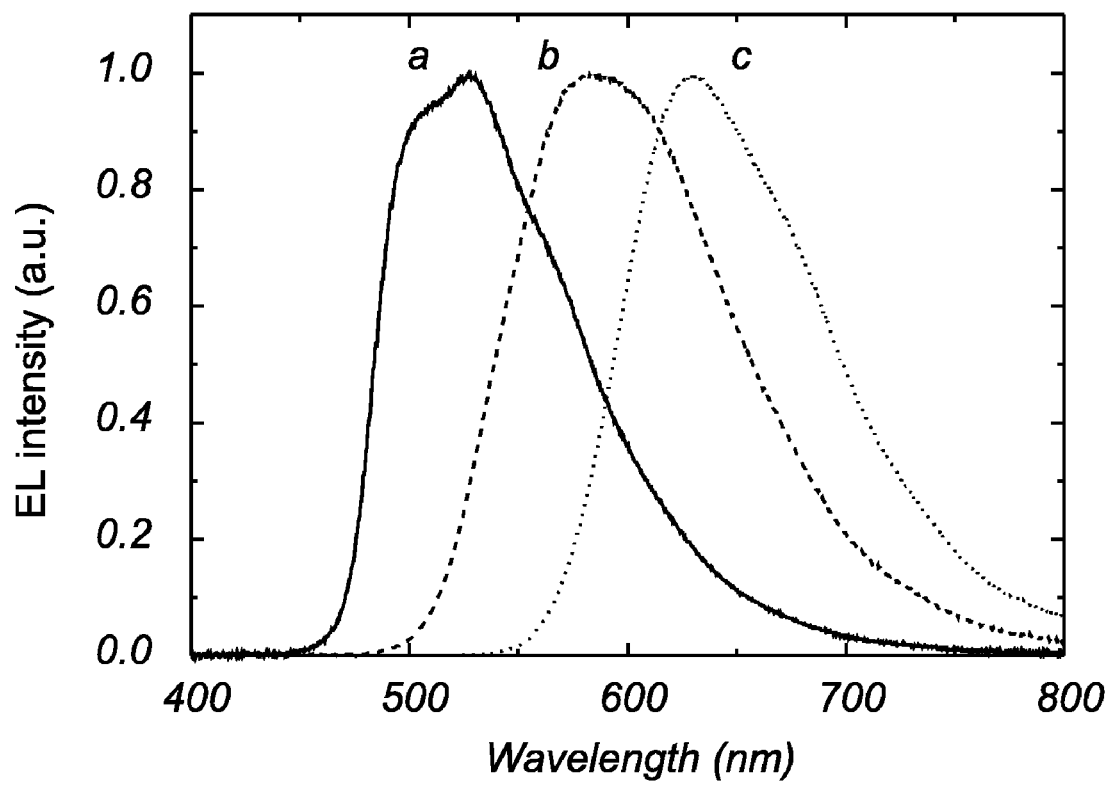
FIG. 3 shows the electro luminescence spectra of ITO/EL layer/Ag devices, where the EL layer consists of $[Ir(ppy)_2,4'-dma-bpy)]^+(PF_6^-)$ (a), $[Ir(ppy)_2(bpy)]^+(PF_6^-)$+PMMA (b), and $[Ru(bpy)_3]^{2+}(PF_6^-)_2$+PMMA (c). The EL intensities are scaled.

Charged Ir complexes starting from Ir(ppy)$_3$ can be obtained by replacing one 2-phenylpyridine ligand with bipyridine. The reported cationic complexes of this type [Ir(ppy)$_2$(bpy)] show emission in the yellow region (FIG. 3b and [6]) due to lower LUMO orbitals of the bpy ligand compared to the 2-phenylpyridine. The present inventor's success in tuning emission spectral properties of the cationic complexes in the blue region comes with meticulous selection of the ligands having LUMO orbitals energy comparable to the 2-phenylpyridine. As an example; by attaching dimethylamino donor groups to the bipyridine ligand, the LUMO level increases again to the same value as for Ir(ppy)$_3$ while at the same time the HOMO level decreases significantly, resulting in a blue shift of the emission maximum (see complex 3-1 of Example 3 below). Further blue shift in mixed ligand complexes was obtained by introducing acceptor groups (2,4-difluoro) on the phenyl ring of 2-phenylpyridine (complexes 3-6 and 3-9 of Example 3 below), which stabilizes the HOMO orbitals without significantly influencing the LUMO orbitals, leading to further increase in HOMO-LUMO gap compared to complex 3-1 and Ir(ppy)$_3$.

Also, the emission spectra of the cationic iridium complexes were shifted into the red region by introducing acceptor groups on the pyridine of 2-phenylpyridine, which stabilize significantly the LUMO orbitals, consequently decreasing the HOMO-LUMO gap leading to red emission. Examples of acceptor groups are $CO_2CH_3$ (e.g. complexes 3-3, and 9-2 of Example 3 below) and substituted styryl (all complexes 14, and e.g. 3-4 and 9-3 of Example 3 below).

In anionic complexes (see complexes 1, 2, 5 and 6 of Example 3 below) shift of the emission spectra into the deep blue region was achieved by further increasing the gap between the HOMO and the LUMO levels through introducing the auxiliary ligand $CN^-$ or $NCS^-$, by replacing one 2-phenylpyridine ligand from Ir(ppy)$_3$, which induces a strong ligand field splitting and thus an increase in HOMO-LUMO gap (compare complex 1-6 with 3-6 of Example 3 below). In these complexes, the energy of the LUMO orbitals is similar to the neutral complexes. However, the energy of the HOMO orbitals is stabilized by acceptor $CN^-$ or $NCS^-$ ligands resulting in significantly blue shifted emission.

The highest triplet quantum yields of iridium complexes containing 2-phenylpyridine ligands are due to several factors: (a) Iridium has large d-orbital splitting compared to other metals in the series. (b) Strong ligand field strength of phenyl anion ligand that increases the energy between $t_{2g}$ and $e_g$ orbitals leading to enhanced gap between the $e_g$ and LUMO of the ligand. (c) Close lying—* and MLCT states together with the heavy atom effect that enhances the spin-orbit coupling. The even more effective strategy to magnify the quantum yields of this class of complexes is to increase further the gap between the $e_g$ and LUMO orbitals by introducing the ligands such as $CN^-$ and $NCS^-$, which are known to have strong ligand field stabilization energy. In such type of complexes, the charge transfer excited states decay through radiative pathways.

A metal complex according to the present invention can be generally described as a complex comprising a metal atom and ligands, which bind to the metal atom. Examples of metals to be used in metal complexes according to the present invention are Ir, Os, Ru, Pt, Pd, Re and Zn. The metal complexes according to the invention suitably comprise an Ir-atom.

The number of ligands will vary depending on the number of binding sites of the metal atom. For example, Ir has six binding sites, and Pt has four binding sites.

As described above, the ligands tune the emission wavelength by the proper substitutions.

The non-substituted positions, i.e. the non-specified substitution positions, could in principle constitute any chemical moiety, but normally, the non-substituted positions are H. However, the non-substituted positions may also be e.g. alkyl or aryl.

One preferred metal complex according to the invention is [Ir(ppy)$_2$(4,4'-dma-bpy]$^+$(PF$_6^-$) (complex 3-1 of Example 3, FIG. 2a). This metal complex is obtained by attaching tertiary amine groups to the bipyridine ligand of [Ir(ppy)$_2$(bpy)]$^+$ (PF$_6^-$) (FIG. 2b), which normally emits in yellow. [Ir(ppy)$_2$(4,4'-dma-bpy]$^+$(PF$_6^-$) has similar properties as [Ir(ppy)$_2$(bpy)]$^+$(PF$_6^-$), i.e. it exhibits electro luminescence and provide mobile ions, so that it can be applied in a LEEC.

The difference between [Ir(ppy)$_2$(4,4'-dma-bpy]$^+$(PF$_6^-$) (complex 3-1 of Example 3 below) and [Ir(ppy)$_2$(bpy)]$^+$ (PF$_6^-$) is that the emission of the first is blue-shifted by about 70 nm due to the amine substitution. This can be seen in FIG. 3, which shows the electro luminescence spectra of devices with complex 3-1 (a) and with [Ir(ppy)$_2$(bpy)]$^+$(PF$_6^-$) (b). Spectrum c of a device made with [Ru(bpy)$_3$]$^{2+}$(PF$_6^-$)$_2$ (see FIG. 2 structure c) is added as a reference.

Other preferred metal complexes according to the invention are the following complexes of Example 3 below: 1-5, 1-6, 1-9, 2-5, 2-6, 2-9, 3-2, 3-3, 3-6, 3-9, 4-6, 5-1, 9-2, 9-3, 9-4, 10-4, 11-1, 12-1, 13-5 and 14-1.

The band gap-increasing effect of the amine substitution is applicable not only on charged but also on neutral Ir complexes. This means that this approach to obtain blue-emitting triplet emitters can also be used for OLEDs, based on polymers as well as small molecules.

In OLEDs, a neutral complex is preferably used, which is dissolved in a small concentration in a suitable host, which can be a semi-conducting polymer, e.g. PVK, or a semi conducting small molecule, e.g. Alq$_3$.

The complex 3-1 is one example of Ir complexes with blue shifted phosphorescence at room temperature due to meticulous selection of the ligands containing donor substituents, in this case dimethylamine, which increases the energy of the lowest unoccupied molecular orbitals (LUMO). The resulting complexes of these ligands show an increased gap between the LUMO of the substituted ligand and the metal $t_{2g}$ orbitals ensuing a blue shift of the emission maxima. The gap between the LUMO of the ligands and the metal $t_{2g}$ orbitals can be effectively controlled by the number and kind of donor and acceptor groups. Moreover, the increased gap between the ligand LUMO and metal $e_g$ orbitals decrease the non-radiative pathways leading to very high quantum yields in solution at room temperature with long lifetimes.

Figure 4A:
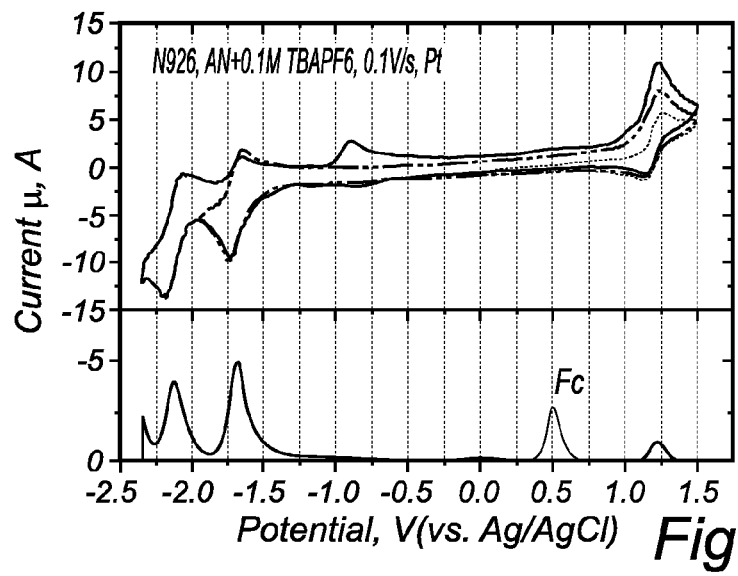
FIG. 4 shows electrochemical data of three representative complexes according to the invention showing the separation between the reduction (LUMO) and oxidation (HOMO) potentials. (The complexes shown are: N926, corresponding to complex 3-1 {$[Ir(ppy)_2(4,4'-dma-bpy)]^+(PF_6^-)$} of Example 3 below; N958, corresponding to complex 9-2 of Example 3 below; and N951, corresponding to complex 9-1 of Example 3 below.)
Figure 4B:
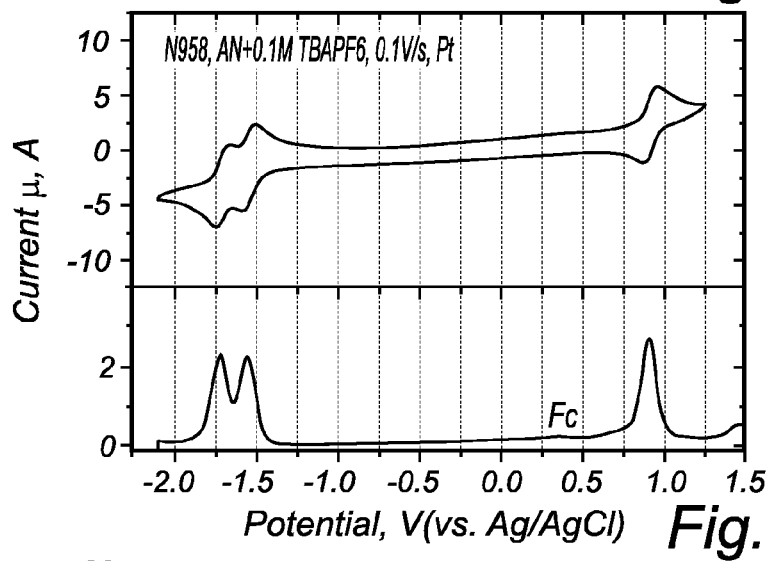
Figure 4C:
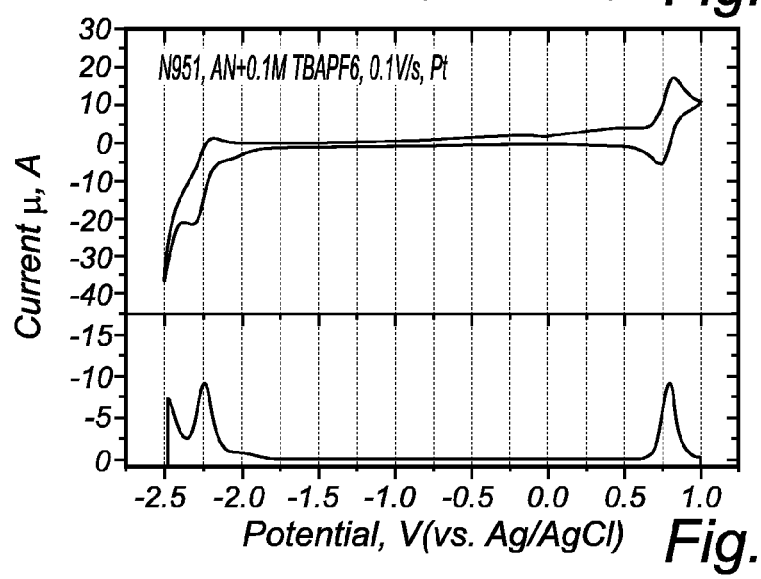

FIG. 4 shows electrochemical data of three representative complexes according to the invention showing the separation between the reduction (LUMO) and oxidation (HOMO)

potentials. (The complexes shown are: N926, corresponding to complex 3-1 {[Ir(ppy)$_2$(4,4'-dma-bpy)]$^+$(PF$_6^-$)} of Example 3 below; N958, corresponding to complex 9-2 of Example 3 below; and N951, corresponding to complex 9-1 of Example 3 below.)

The present invention is in no way limited to blue-emitting complexes, but encompasses the tuning of the emission wavelength of a wide variety of transition metal complexes to different colors by using certain substituents.

The invention can in principle be applied in any organic light-emitting device, for display as well as for lighting applications. When applied in a LEEC the most relevant application is in large-area lighting systems, optionally colour-tunable, for example for atmosphere creation, for car interior lighting (roof, walls, dashboard), for decorative lighting, and for in- and outdoor signage.

As used herein, a "light-emitting device" refers to a device comprising at least two electrodes, in between which is placed a material or blend of materials capable of electroluminesence.

Suitable materials for use as an electrode according to the invention are e.g. Au, Ag, Al, Ba, Ca, LiF, Pt, Cu, Zn, Ni, Fe, Pb, In, W, Pd, indium tin oxide (ITO), indium zinc oxide, lead oxide, tin oxide, graphite, doped silicon, doped germanium, doped gallium arsenide, doped polyalinine, doped polypyrrole, doped polythiophene, and derivatives and mixtures thereof. Other suitable electrode materials are well known to a man skilled in the art. In addition, alloys of the previously mentioned materials may be used as an electrode according to the present invention.

Both electrodes can in principle be the cathode or the anode. The cathode is defined as the electron-injecting electrode, while the anode is the hole-injecting electrode.

The term "anode" as used herein refers to an electrically conductive layer, which is used as electrode for hole injection into the electro luminescent material under appropriate biasing conditions.

An anode according to the invention may be structured, e.g. segmented into separately addressable pixels or connected in series or parallel or intact, possibly with additional thick metal strips for uniform shunting of the currents over large areas. The term "cathode" as used herein refers to an electrically conductive layer, which is used as electrode for electron injection into the electro luminescent material under appropriate biasing conditions.

A cathode according to the invention may be structured or intact, e.g. segmented into separately addressable pixels, or connected in series or parallel or intact, possibly with additional thick metal strips for uniform shunting of the currents over large areas.

In a light-emitting device according to the invention the electro luminescent material is arranged between an anode and a cathode. By the term "arranged between", in this context, is meant that the electro luminescent material is electrically in contact with the anode and the cathode in such a way that holes and electrons can be introduced into the electro luminescent material and electro luminescence is achieved, under appropriate biasing conditions. For example, the electro luminescent material may be sandwiched between two electrode layers.

According to the present invention, the electro luminescent material may be mixed with e.g. polymethylmethacrylate, PMMA, in order to improve film formation. Other polymethacrylates could also be added to the electro luminescent material, as well as polyacrylates, polyethers, such as polyethylene oxide or polyethylene glycol, polyesters such as polycarbonates, polyolefines such as Zeonex™, polystyrenes, polysiloxanes or mixtures or derivatives thereof.

The electro luminescent material may also be doped in a semi conducting organic material. This semi conducting organic material can be a polymer or a small molecule. Examples of suitable semi conducting polymers include those comprising a phenylenevinylene, a phenylene, a thiophene, a thienylvinylene, a fluorene or 9,9'-spirobifluorene unit. Polymers like polyphenylethylene, polyquinoxaline, polyvinylcarbazole, or copolymers or blends thereof can also be used. Optionally such polymers are copolymerized or mixed with hole- or electron-transporting moieties such as triarylamines and oxadiazoles.

The thickness of the electro luminescent material arranged between the electrodes may vary. For example, the thickness may be in the range of 5 nm to 1 cm, or in the range of 5 nm to 1 mm, or in the range of 10 nm to 0.1 mm.

In the method for manufacturing a light-emitting device according to the invention, the light-emitting device may be manufactured on a glass substrate. Suitable substrates may be rigid or mechanically flexible and include, beside glass, metals, alloys and plastics. Examples of flexible substrates include PET foil glued temporarily on a carrier substrate, flexible steel foils, silicon, and silicon oxide.

EXAMPLES

Example 1

Synthesis of [Ir(ppy)$_2$(4,4'dma-bpy)]PF$_6^-$ (complex 3-1), where ppy=2-phenylpyridine and dma-bpy=4, 4'-dimethylamino-2,2'-bipyridine The dimeric iridium (III) complex [Ir(ppy)$_2$(Cl)]$_2$(300 mg; 0.28 mM) was dissolved in 100 ml of dichloromethane solvent under nitrogen. To this solution was added 4,4'-dimethylamino-2,2'-bipyridine ligand (176 mg, 0.724 mM). The reaction mixture was refluxed under nitrogen for three 3 days (three hours is sufficient). The solvent dichloromethane was evaporated and the resulting solid was dissolved in 5 mL of methanol. Then, by adding hexafluorophosphate salt solution in methanol [Ir(ppy)$_2$(4,4'dma-bpy)]PF$_6^-$ (complex 3-1) was precipitated. Yield: 306 mg; 50%.

Example 2

Use of [Ir(ppy)$_2$(4,4'dma-bpy)]PF$_6^-$ (complex 3-1) as an Electro Luminescent Material

[Ir(ppy)$_2$(4,4'-dma-bpy)]$^+$(PF$_6^-$) (complex 3-1) was synthesised, and 37.1 mg of the complex was dissolved in 1.855 ml acetonitrile by stirring at 50° C. for 30 min. Thus the concentration of complex in acetonitrile was 20 mg/ml. The solution was brought into a nitrogen atmosphere glovebox, where all subsequent processing was carried out. Molecular sieves were added in order to remove traces of water. After 30 min. the solution was filtrated and spincoated on glass substrates with structured ITO, which had been thoroughly cleaned beforehand using soap, water, isopropanol, ultrasound and UV-ozone. This resulted in homogeneous films of nearly 100 nm thick.

Figure 5:
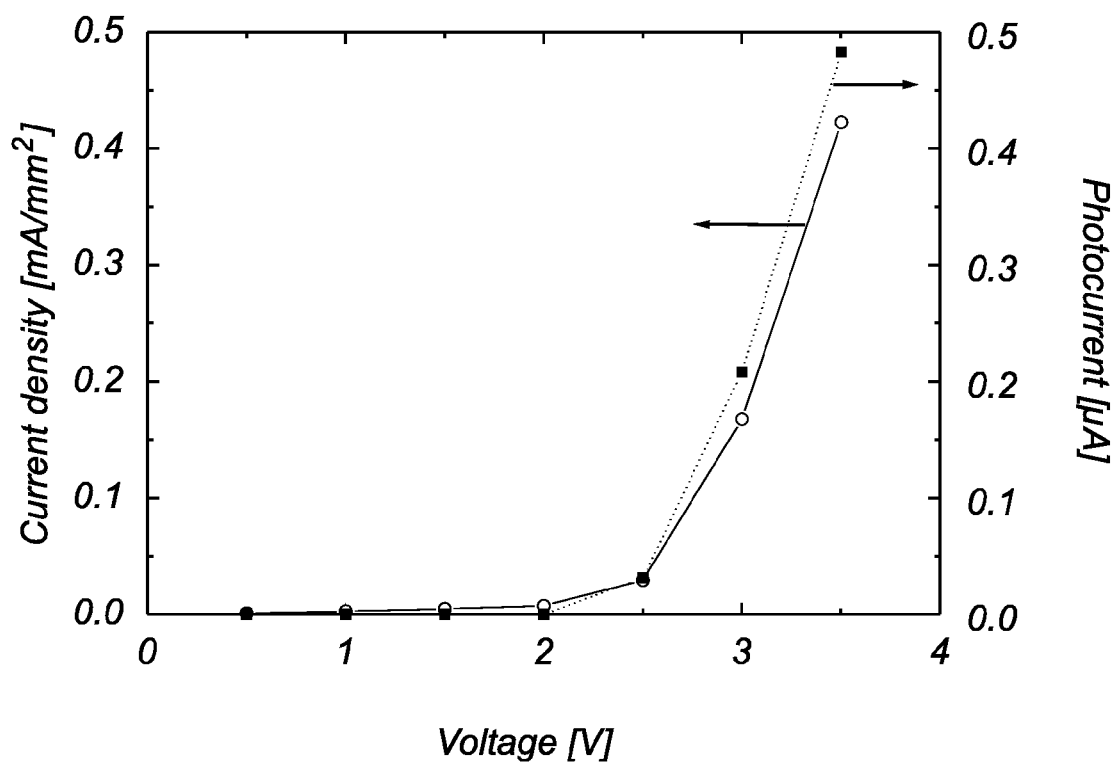
FIG. 5 shows the current density (open circles) and photocurrent (filled squares) versus voltage for an ITO/[Ir(ppy)_2(4,4'-dma-bpy)]^+(PF_6^-)/Ag LEEC, as measured in steady-state situation. The traces are guides-to-the-eye.
Figure 6:
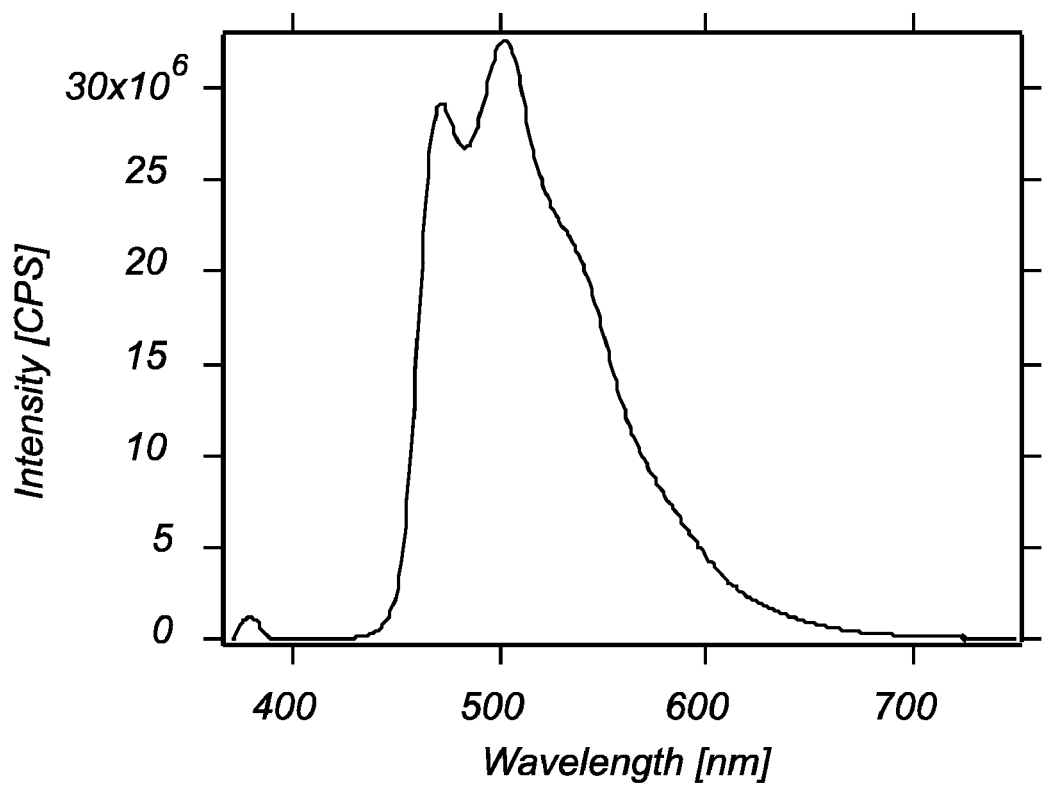
FIG. 6 shows the photoluminescence spectrum in solution for the complex 1-2 of Example 3 below.
Figure 7:
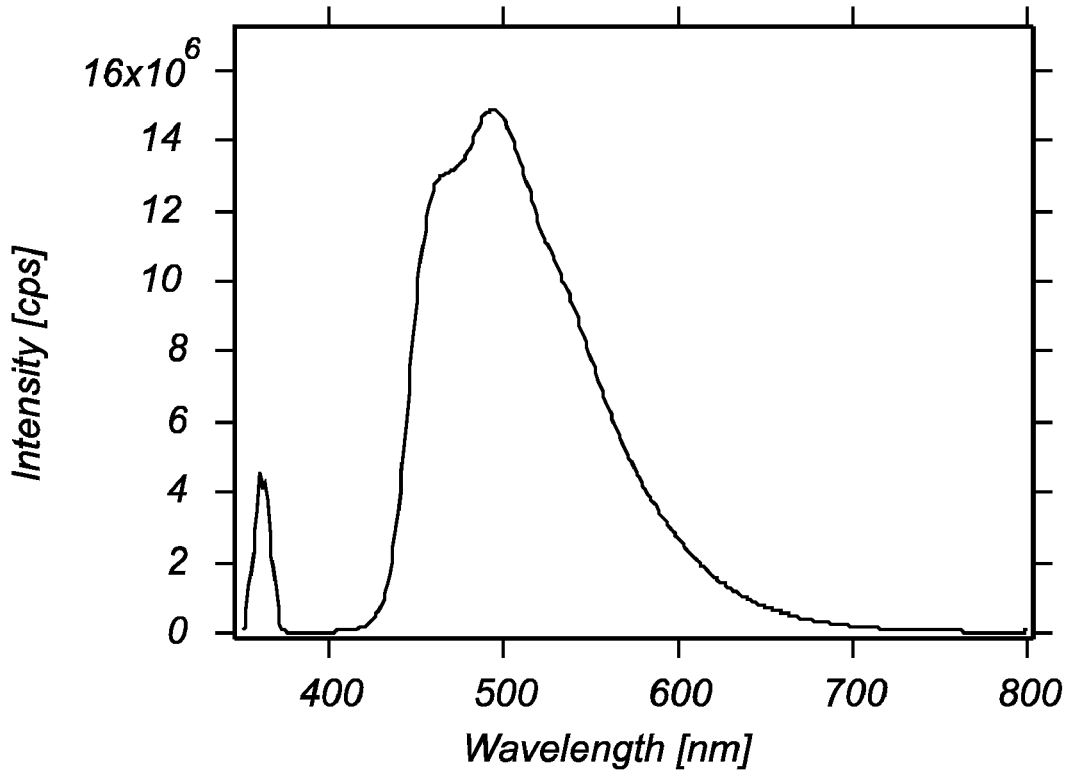
FIG. 7 shows the photoluminescence spectrum in solution for the complex 1-5 of Example 3 below.
Figure 8:
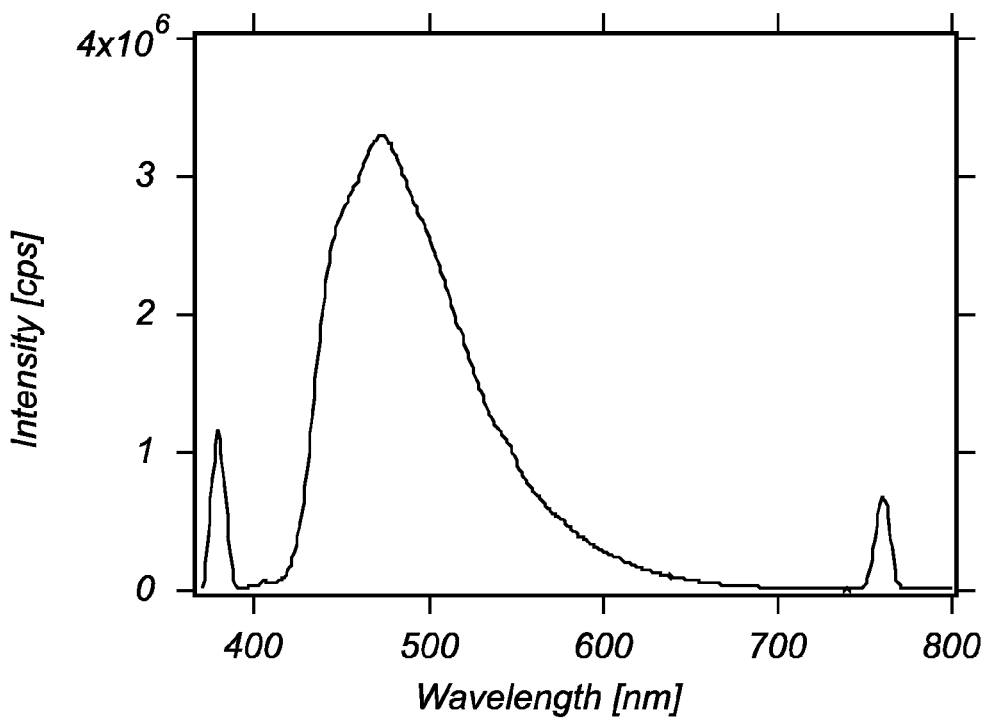
FIG. 8 shows the photoluminescence spectrum in solution for the complex 1-6 of Example 3 below.

The films were dried at 100° C. in nitrogen for about ½ hour. A 100 nm thick Ag electrode was evaporated on top in a vacuum chamber at about $10^{-7}$ mbar at a rate of 0.5 nm/s. This resulted in 4 LEEC devices per substrate. On one of them a voltage of +5 V (i.e. ITO biased positively) was applied until a steady light-emission level was reached. Next, current and photocurrent as a function of voltage were measured by going from high to low voltage and letting the system reach steady state at every voltage. The results are shown in FIG. 5.

Figure 9:
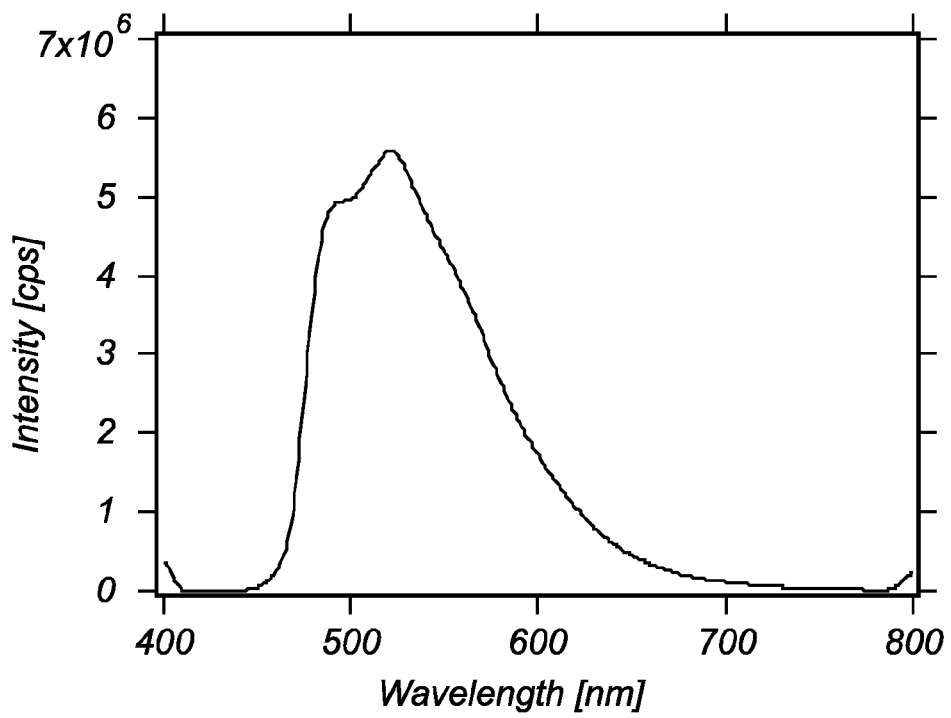
FIG. 9 shows the photoluminescence spectrum in solution for the complex 3-1 of Example 3 below.
Figure 10:
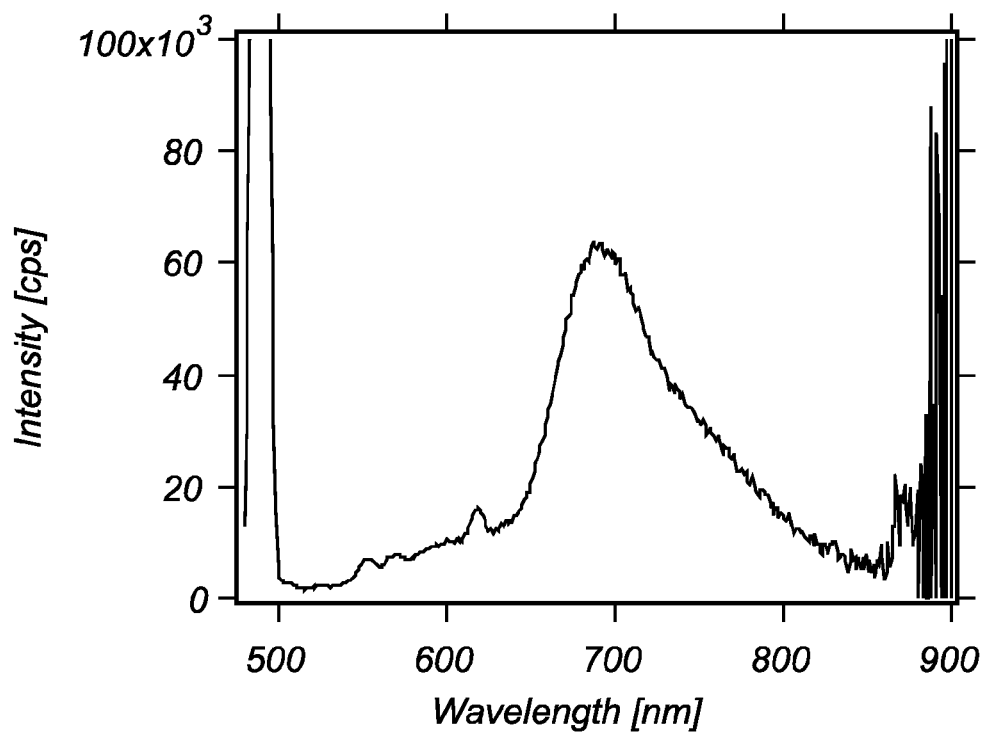
FIG. 10 shows the photoluminescence spectrum in solution for the complex 3-4 of Example 3 below.
Figure 11:
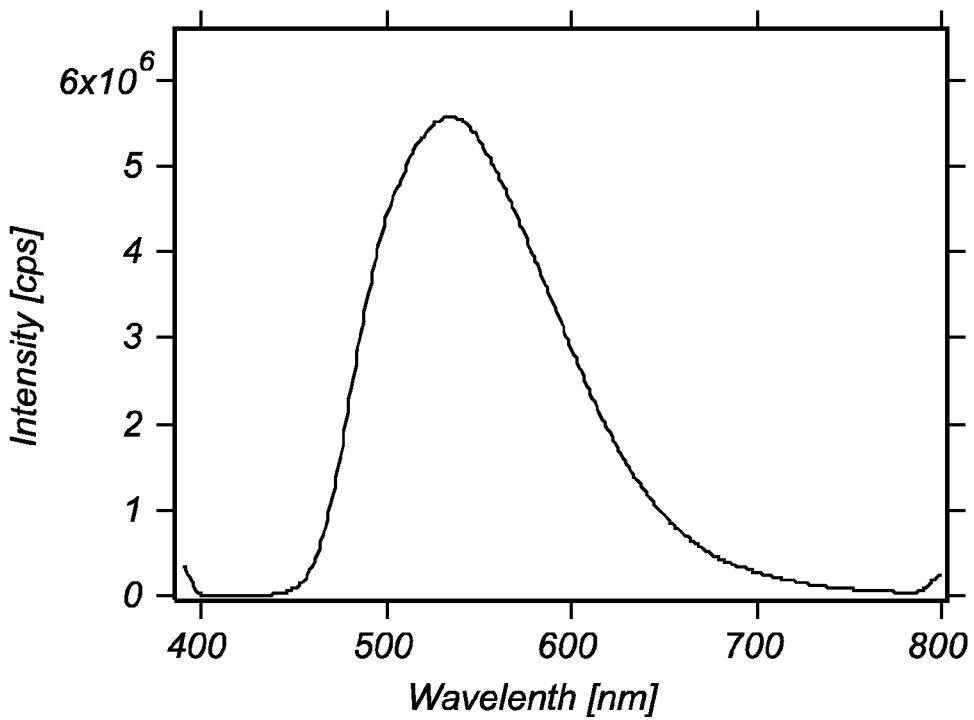
FIG. 11 shows the photoluminescence spectrum in solution for the complex 3-6 of Example 3 below.
Figure 12:
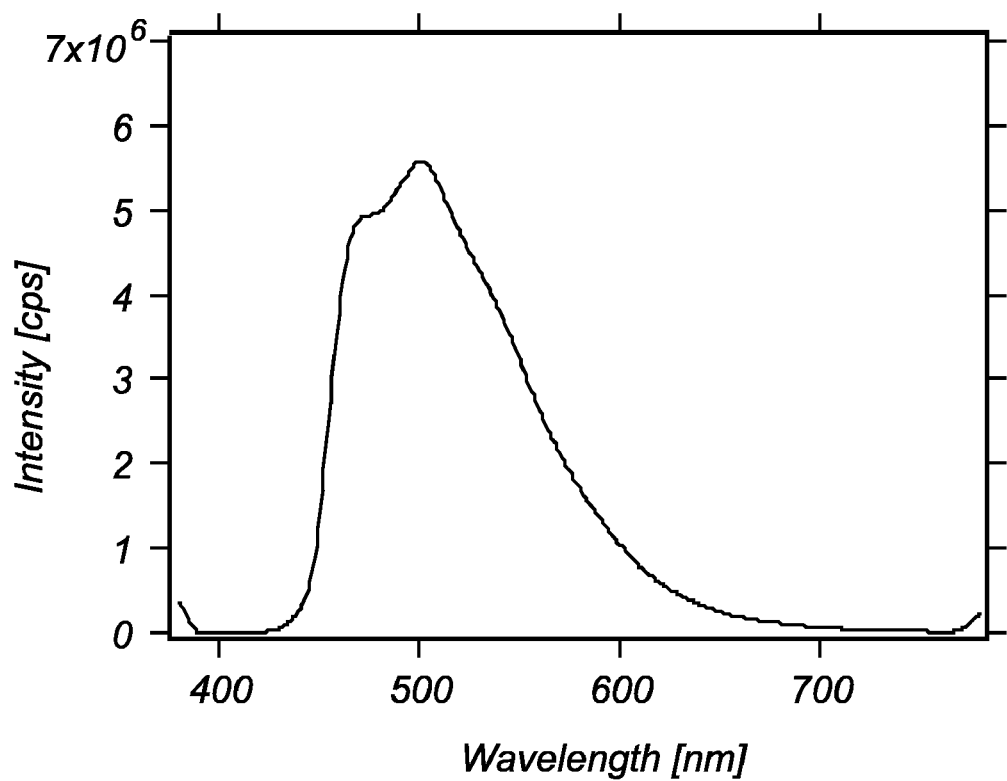
FIG. 12 shows the photoluminescence spectrum in solution for the complex 3-9 of Example 3 below.
Figure 13:
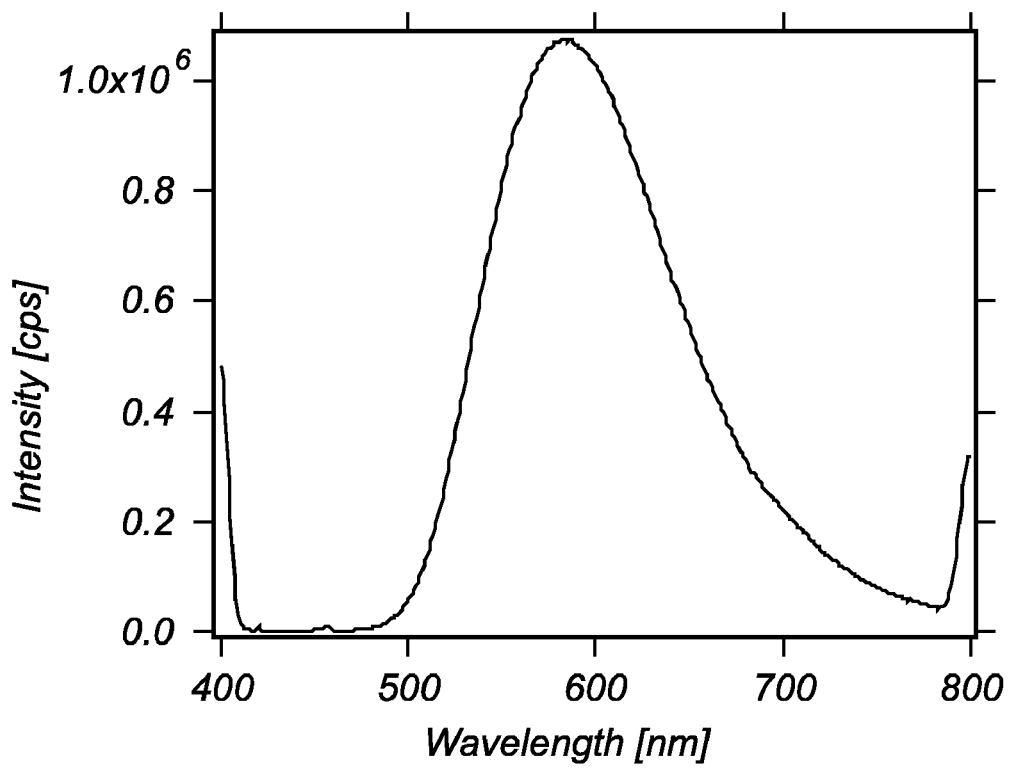
FIG. 13 shows the photoluminescence spectrum in solution for the complex 4-1 of Example 3 below.
Figure 14:
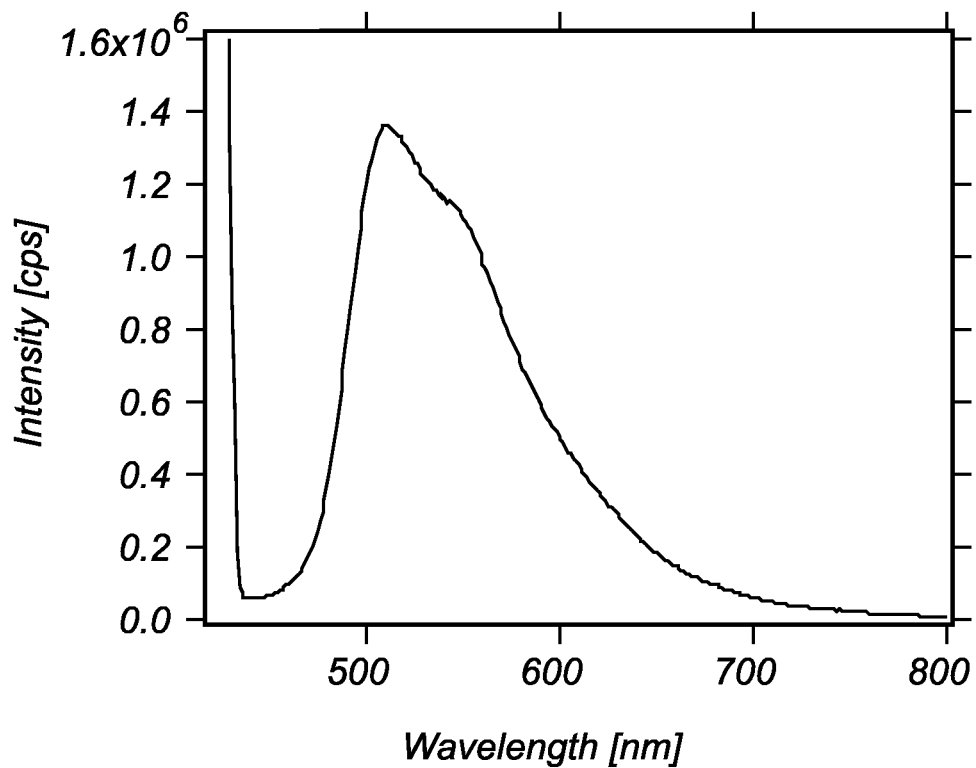
FIG. 14 shows the photoluminescence spectrum in solution for the complex 9-1 of Example 3 below.
Figure 15:
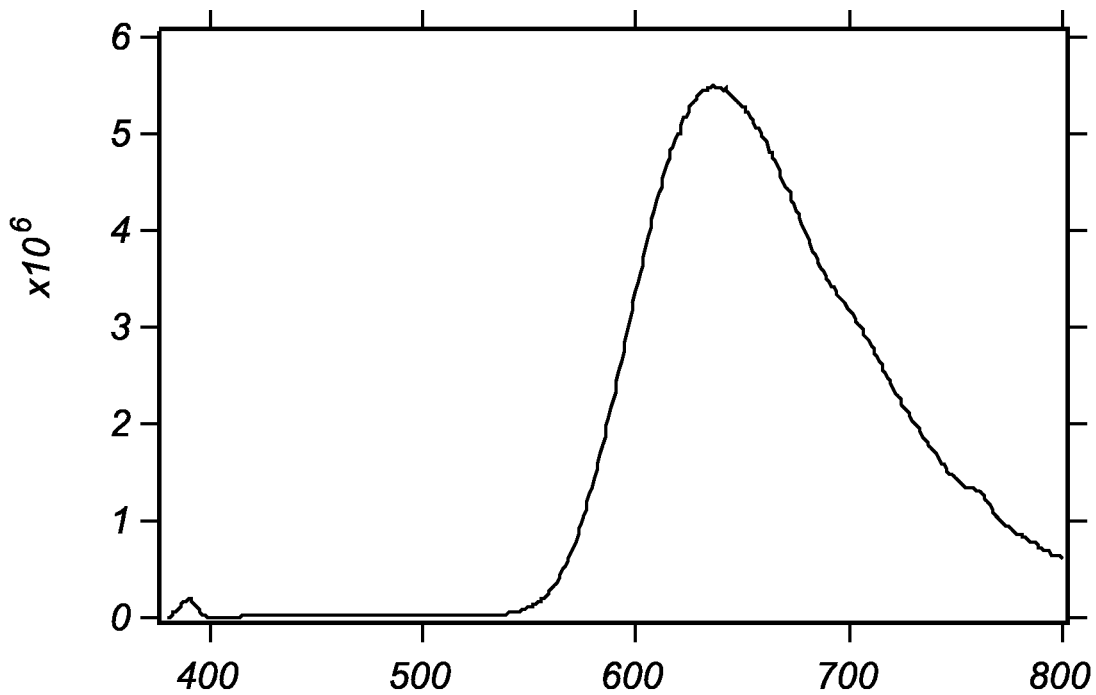
FIG. 15 shows the photoluminescence spectrum in solution for the complex 9-2 of Example 3 below.
Figure 16:
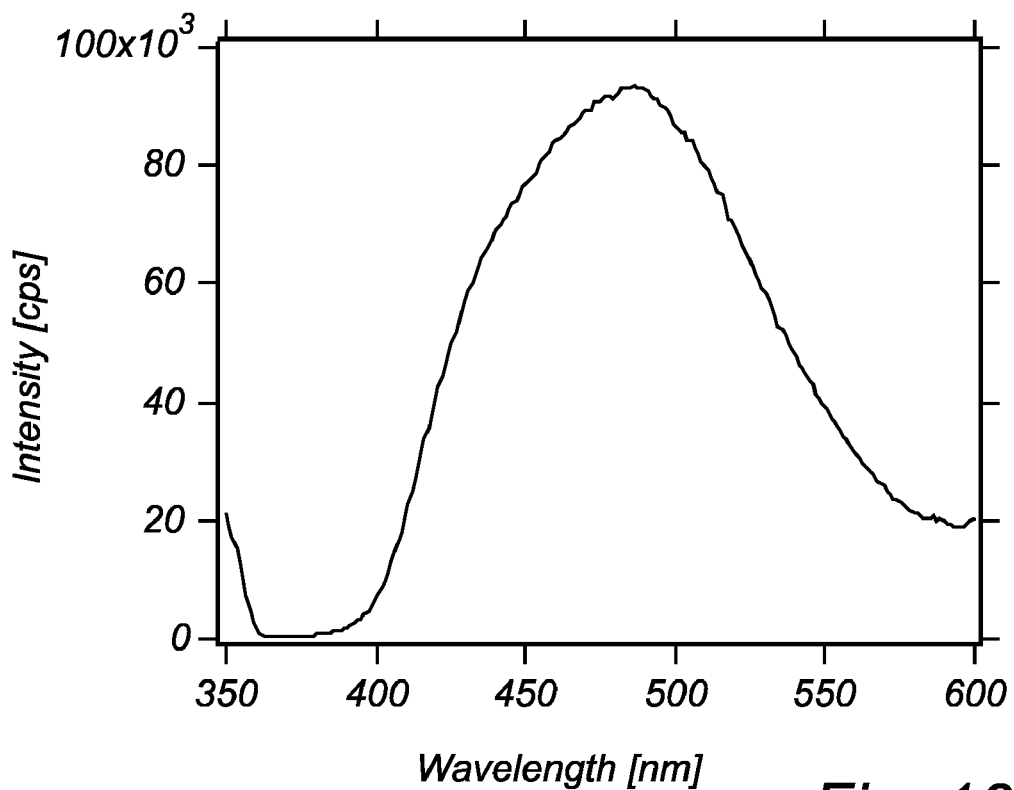
FIG. 16 shows the photoluminescence spectrum in solution for the complex 9-3 of Example 3 below.
Figure 17:
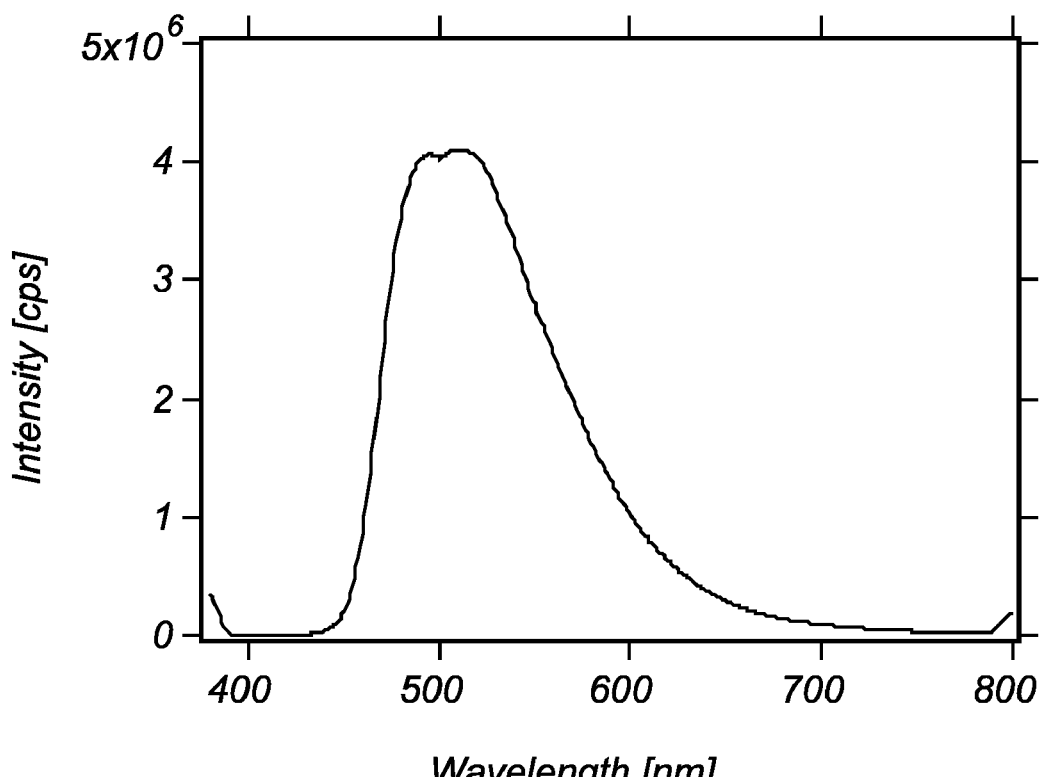
FIG. 17 shows the photoluminescence spectrum in solution for the complex 9-4 of Example 3 below.
Figure 18:
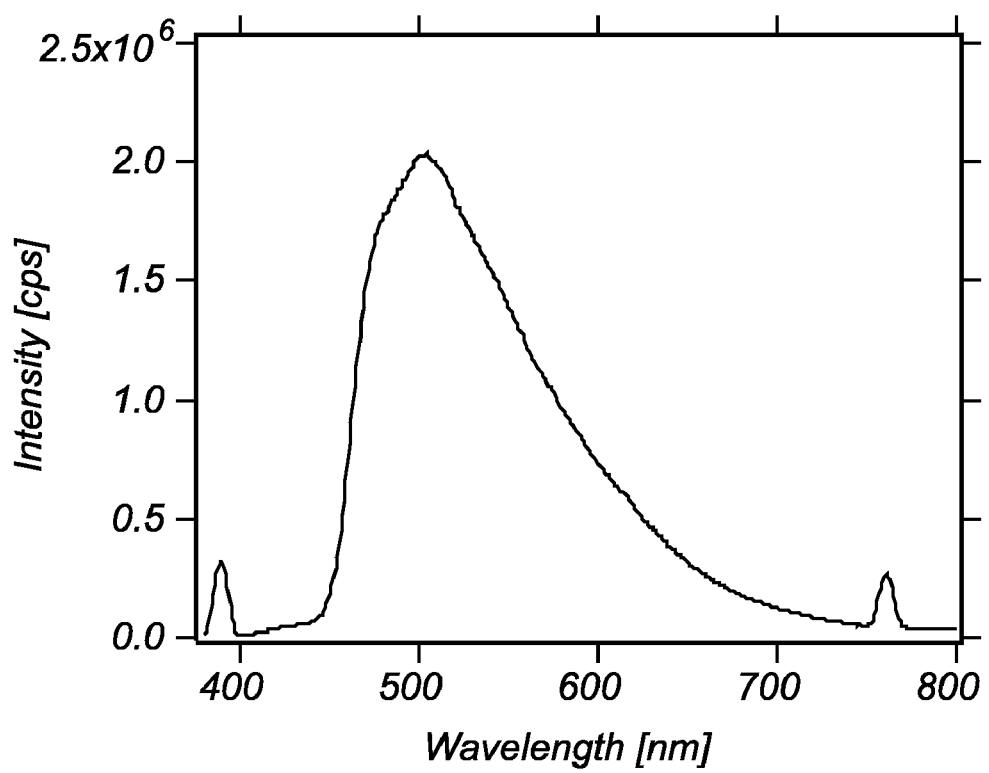
FIG. 18 shows the photoluminescence spectrum in solution for the complex 9-5 of Example 3 below.
Figure 19:
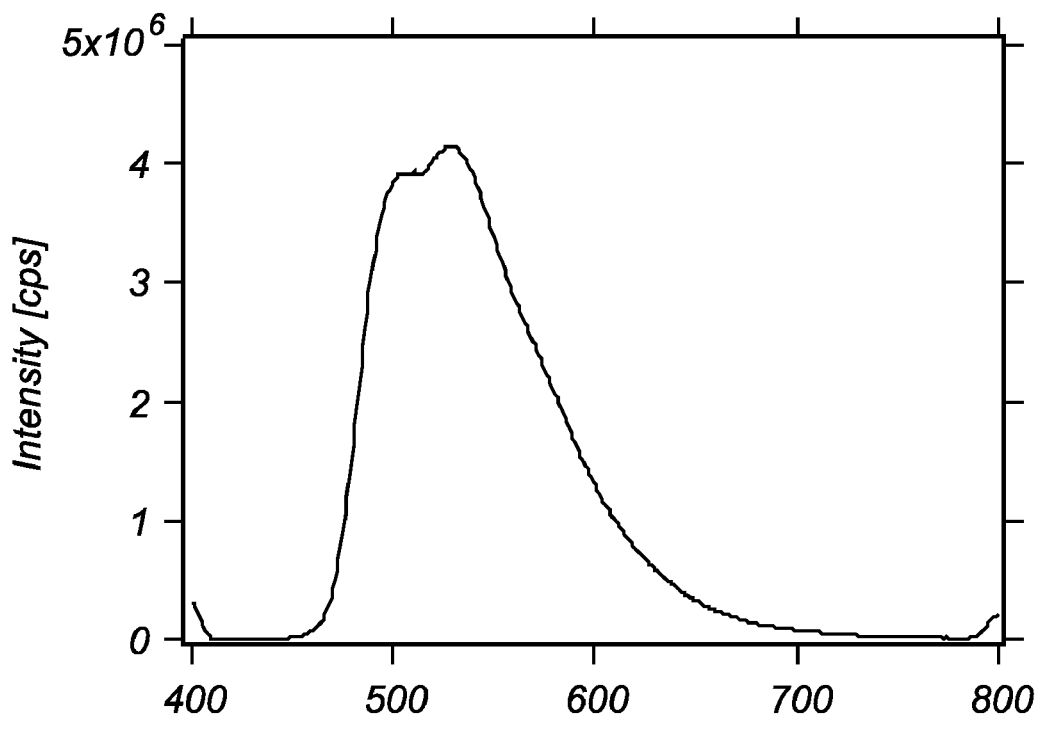
FIG. 19 shows the photoluminescence spectrum in solution for the complex 9-6 of Example 3 below.
Figure 20:
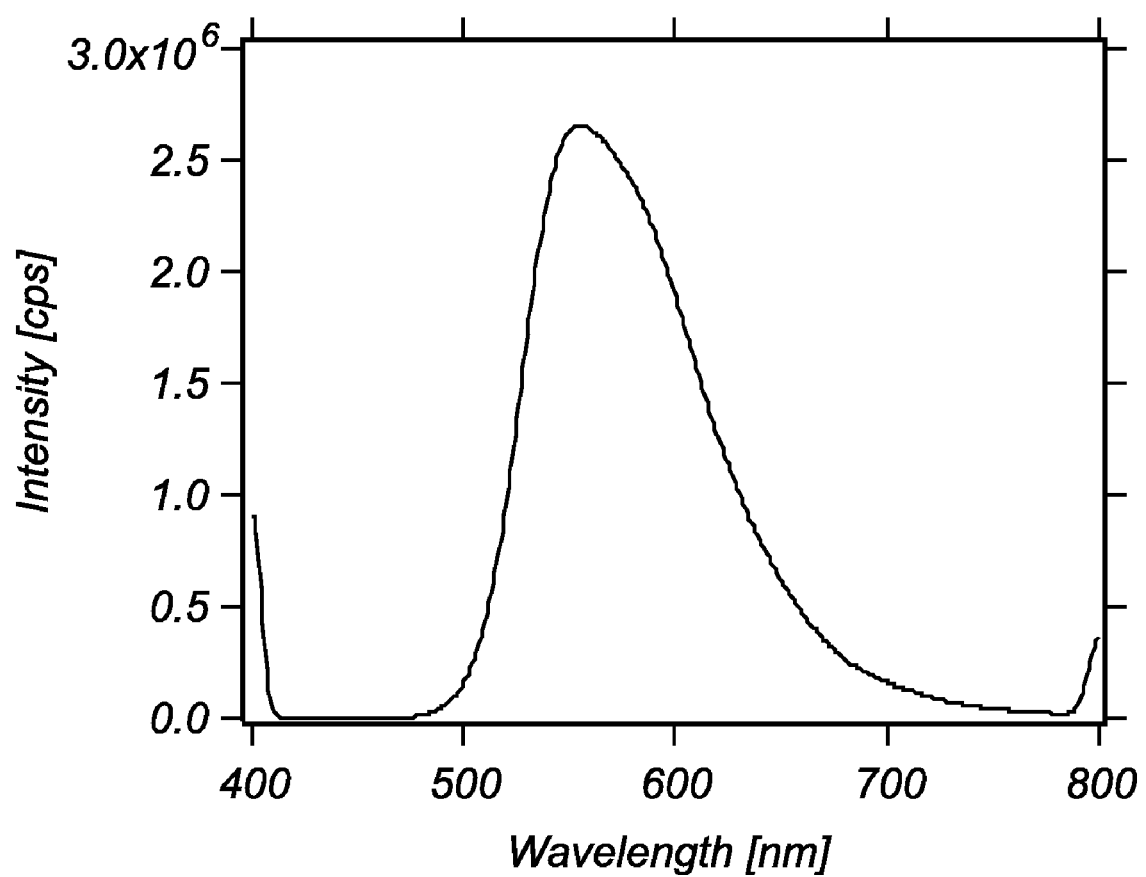
FIG. 20 shows the photoluminescence spectrum in solution for the complex 9-7 of Example 3 below.

The onset voltage for light emission is around 2-2.5 V. The fact that nearly blue emission is obtained with an Ag cathode at such low voltage indicates LEEC behaviour. The electro luminescence spectrum (FIG. 3 trace a) is equal to the photoluminescence spectrum recorded for a film of $[Ir(ppy)_2(4,4'\text{-dma-bpy})]^+(PF_6^-)$ (complex 3-1) on glass, and nearly equal to the photoluminescence spectrum of complex 3-1 in solution (FIG. 9). The photocurrent of 0.48 μA obtained at 3.5 V corresponds to a luminance of around 145 cd/m². However this is only an estimation since the photodiode has not been calibrated with a luminance meter for this particular spectral response. The light output is not very high due to concentration quenching, since the Ir complex is the sole component of the active layer. When the complex is used as a dopant, as in OLEDs, the light output and the efficiency will be much higher.

Example 3

List of Complexes

The 2, 3, 4, 5 positions on the phenyl ring of 2-phenylpyridine are defined as in formula (I).

Complexes 1 and 2:

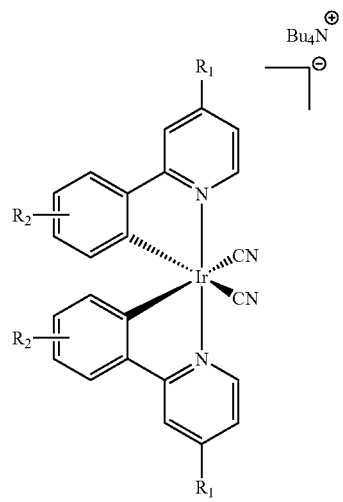

1-1: $R_1$ = H; $R_2$ = H
1-2: $R_1$ = $CH_3$; $R_2$ = H
1-3: $R_1$ = $CO_2CH_3$; $R_2$ = H
1-4: $R_1$ = 4-dimethylaminostyryl; $R_2$ = H
1-5: $R_1$ = $N(CH_3)_2$; $R_2$ = H
1-6: $R_1$ = $N(CH_3)_2$; $R_2$ = 2,4-difluoro
1-7: $R_1$ = $N(CH_3)_2$; $R_2$ = 3,5-difluoro
1-8: $R_1$ = $N(CH_3)_2$; $R_2$ = 3-$OCH_3$
1-9: $R_1$ = H; $R_2$ = 2,4-difluoro

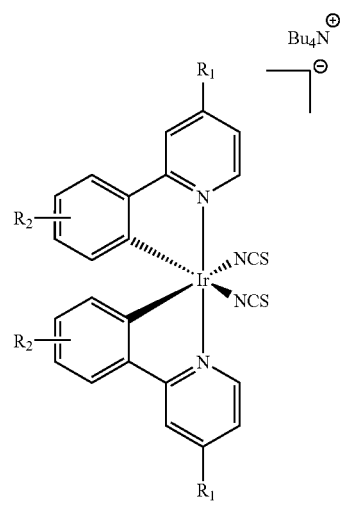

2-1: $R_1$ = H; $R_2$ = H
2-2: $R_1$ = $CH_3$; $R_2$ = H
2-3: $R_1$ = $CO_2CH_3$; $R_2$ = H
2-4: $R_1$ = 4-dimethylaminostyryl; $R_2$ = H
2-5: $R_1$ = $N(CH_3)_2$; $R_2$ = H
2-6: $R_1$ = $N(CH_3)_2$; $R_2$ = 2,4-difluoro
2-7: $R_1$ = $N(CH_3)_2$; $R_2$ = 3,5-difluoro
2-8: $R_1$ = $N(CH_3)_2$; $R_2$ = 3-$OCH_3$
2-9: $R_1$ = H; $R_2$ = 2,4-difluoro Complexes 3 and 4:

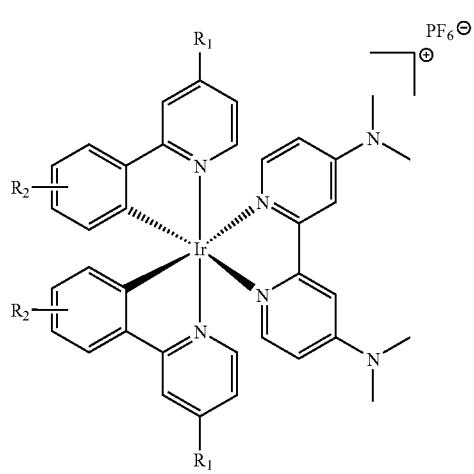

3-1: $R_1$ = H; $R_2$ = H
3-2: $R_1$ = $CH_3$; $R_2$ = H
3-3: $R_1$ = $CO_2CH_3$; $R_2$ = H
3-4: $R_1$ = 4-dimethylaminostyryl; $R_2$ = H
3-5: $R_1$ = $N(CH_3)_2$; $R_2$ = H
3-6: $R_1$ = $N(CH_3)_2$; $R_2$ = 2,4-difluoro
3-7: $R_1$ = $N(CH_3)_2$; $R_2$ = 3,5-difluoro
3-8: $R_1$ = $N(CH_3)_2$; $R_2$ = 3-$OCH_3$
3-9: $R_1$ = H; $R_2$ = 2,4-difluoro

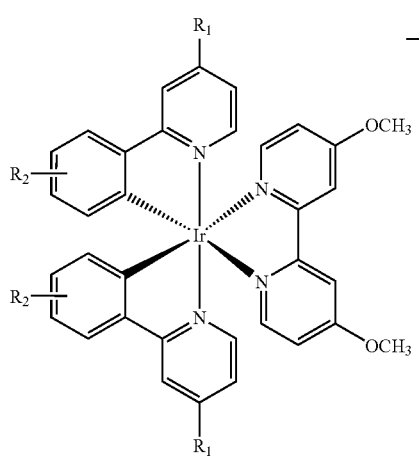

4-1: $R_1 = H; R_2 = H$
4-2: $R_1 = CH_3; R_2 = H$
4-3: $R_1 = CO_2CH_3; R_2 = H$
4-4: $R_1 =$ 4-dimethylaminostyryl; $R_2 = H$
4-5: $R_1 = N(CH_3)_2; R_2 = H$
4-6: $R_1 = N(CH_3)_2; R_2 =$ 2,4-difluoro
4-7: $R_1 = N(CH_3)_2; R_2 =$ 3,5-difluoro
4-8: $R_1 = N(CH_3)_2; R_2 =$ 3-OCH$_3$

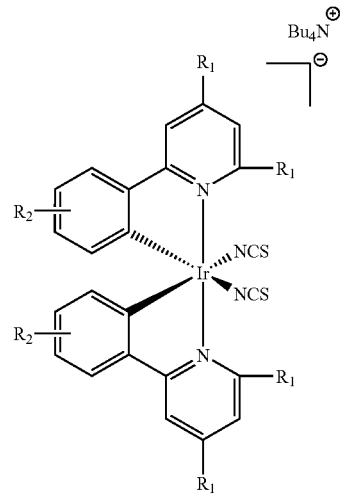

6-1: $R_1 = N(CH_3)_2; R_2 =$ 2,4-difluoro
6-2: $R_1 = N(CH_3)_2; R_2 =$ 3,5-difluoro
6-3: $R_1 = OCH_3; R_2 =$ 2,4-difluoro
6-4: $R_1 = OCH_3; R_2 =$ 3,5-difluoro Complexes 5 and 6:

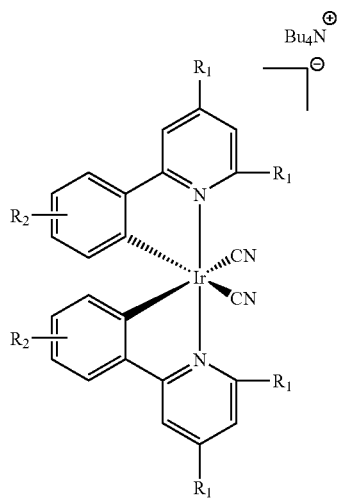

5-1: $R_1 = N(CH_3)_2; R_2 =$ 2,4-difluoro
5-2: $R_1 = N(CH_3)_2; R_2 =$ 3,5-difluoro
5-3: $R_1 = OCH_3; R_2 =$ 2,4-difluoro
5-4: $R_1 = OCH_3; R_2 =$ 3,5-difluoro Complexes 7 and 8:

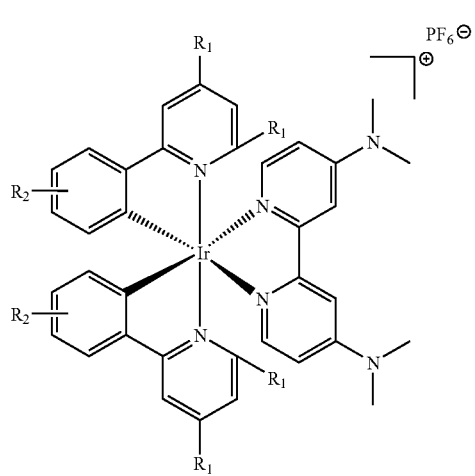

7-1: $R_1 = N(CH_3)_2; R_2 =$ 2,4-difluoro
7-2: $R_1 = N(CH_3)_2; R_2 =$ 3,5-difluoro
7-3: $R_1 = OCH_3; R_2 =$ 2,4-difluoro
7-4: $R_1 = OCH_3; R_2 =$ 3,5-difluoro

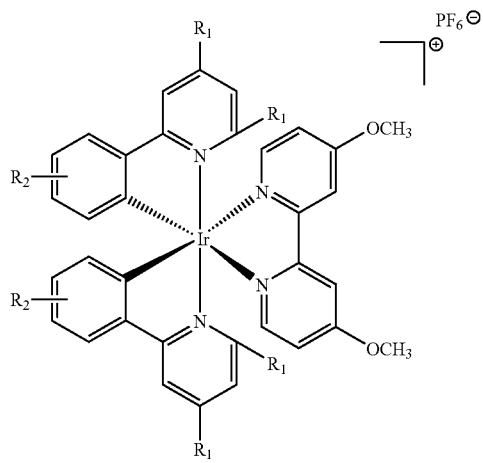

8-1: R₁ = N(CH₃)₂; R₂ = 2,4-difluoro
8-2: R₁ = N(CH₃)₂; R₂ = 3,5-difluoro
8-3: R₁ = OCH₃; R₂ = 2,4-difluoro
8-4: R₁ = OCH₃; R₂ = 3,5-difluoro Complexes 9 and 10:

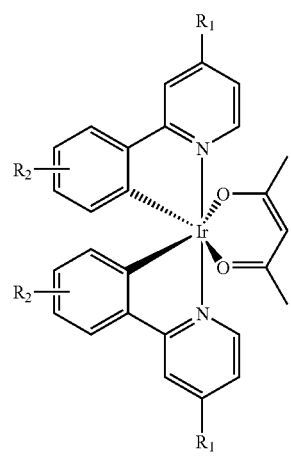

9-1: R₁ = CH₃; R₂ = H
9-2: R₁ = CO₂CH₃; R₂ = H
9-3: R₁ = 4-dimethylaminostyryl; R₂ = H
9-4: R₁ = N(CH₃)₂; R₂ = H
9-5: R₁ = N(CH₃)₂; R₂ = 2,4-difluoro
9-6: R₁ = N(CH₃)₂; R₂ = 3,5-difluoro
9-7: R₁ = N(CH₃)₂; R₂ = 3-OCH₃

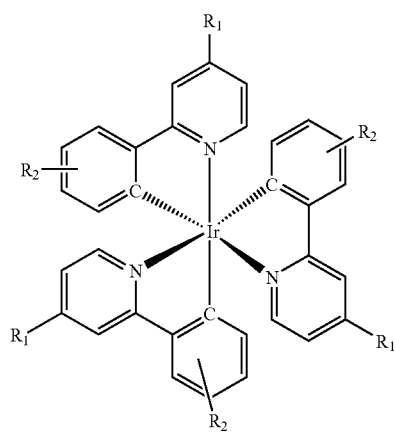

10-1: R₁ = CH₃; R₂ = H
10-2: R₁ = CO₂CH₃; R₂ = H
10-3: R₁ = 4-dimethylaminostyryl; R₂ = H
10-4: R₁ = N(CH₃)₂; R₂ = H
10-5: R₁ = N(CH₃)₂; R₂ = 2,4-difluoro
10-6: R₁ = N(CH₃)₂; R₂ = 3,5-difluoro
10-7: R₁ = N(CH₃)₂; R₂ = 3-OCH₃

Complexes 11 and 12:

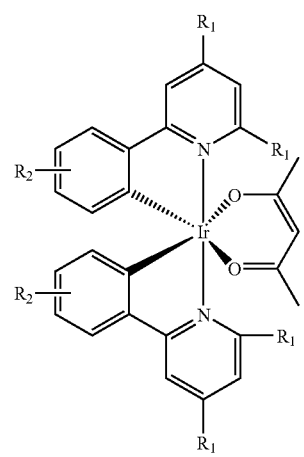

11-1: R₁ = N(CH₃)₂; R₂ = 2,4-difluoro
11-2: R₁ = N(CH₃)₂; R₂ = 3,5-difluoro
11-3: R₁ = OCH₃; R₂ = 2,4-difluoro
11-4: R₁ = OCH₃; R₂ = 3,5-difluoro

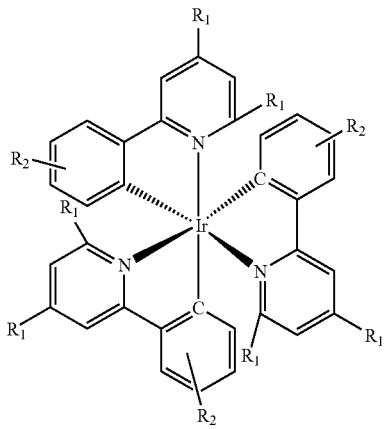

12-1: $R_1$ = N(CH$_3$)$_2$; $R_2$ = 2,4-difluoro
12-2: $R_1$ = N(CH$_3$)$_2$; $R_2$ = 3,5-difluoro
12-3: $R_1$ = OCH$_3$; $R_2$ = 2,4-difluoro
12-4: $R_1$ = OCH$_3$; $R_2$ = 3,5-difluoro Complexes 13 and 14:

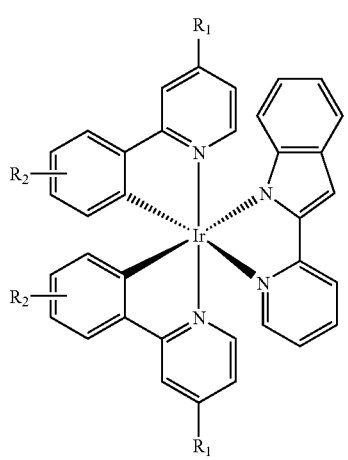

13-1: $R_1$ = H; $R_2$ = H
13-2: $R_1$ = CH$_3$; $R_2$ = H
13-3: $R_1$ = CO$_2$CH$_3$; $R_2$ = H
13-4: $R_1$ = 4-dimethylaminostyryl; $R_2$ = H
13-5: $R_1$ = N(CH$_3$)$_2$; $R_2$ = H
13-6: $R_1$ = N(CH$_3$)$_2$; $R_2$ = 2,4-difluoro
13-7: $R_1$ = N(CH$_3$)$_2$; $R_2$ = 3,5-difluoro
13-8: $R_1$ = N(CH$_3$)$_2$; $R_2$ = 3-OCH$_3$

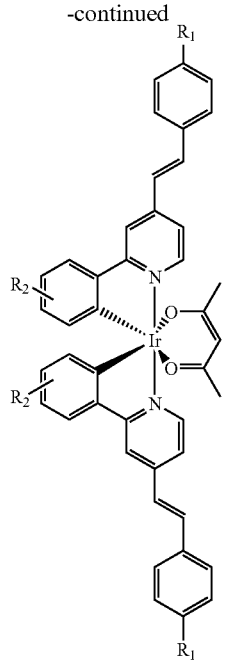

14-1: $R_1$ = H; $R_2$ = H
14-2: $R_1$ = CH$_3$; $R_2$ = H
14-3: $R_1$ = CO$_2$CH$_3$; $R_2$ = H
14-4: $R_1$ = 4-dimethylaminostyryl; $R_2$ = H
14-5: $R_1$ = N(CH$_3$)$_2$; $R_2$ = H
14-6: $R_1$ = N(CH$_3$)$_2$; $R_2$ = 2,4-difluoro
14-7: $R_1$ = N(CH$_3$)$_2$; $R_2$ = 3,5-difluoro
14-8: $R_1$ = N(CH$_3$)$_2$; $R_2$ = 3-OCH$_3$ Example 4

Synthesis Protocols 2-phenyl-4-methylpyridine L1

Crotonaldehyde (2 g, 28.5 mmol) was added to a mixture of phenacylpyridinium chloride (6.2 g, 26 mmol) and NH$_4$OAc (20 g, 260 mmol) in EtOH (150 ml). The resulting solution was refluxed overnight in an open-air apparatus. After being cooled to room temperature, EtOH was evaporated and water (150 ml) and Et$_2$O (150 ml) were added. The organic phase was separated and the water phase extracted with Et$_2$O (150 ml). The combined organic fractions were washed with water (150 ml), brine (150 ml), dried over MgSO$_4$ and evaporated to dryness. The resulting oil was then dissolved in EtOH (10 ml) and conc. HCl (5 ml) was added. The solution was then evaporated to dryness. The obtained solid was dissolved in the minimum volume of EtOH and precipitated by addition of Et$_2$O (200 ml) under rapid stirring. The precipitate was filtered off and washed with small portions of Et$_2$O to afford 3.7 g (69%) of the titled compound in its hydrochloride salt as a slightly brown solid.

$^1$H-NMR (DMSO-d$^6$, 298K, 200 MHz, δ ppm) 2.62 (s, 3H), 7.64 (m, 3H), 7.79 (d, J=5.8 Hz, 1H), 8.13 (m, 2H), 8.29 (s, 1H), 8.73 (d, J=5.8 Hz, 1H). $^{13}$C-NMR (DMSO-d$^6$, 298K, 50 Hz, δ ppm) 22.0, 125.6, 126.1, 128.5, 129.6, 132.0, 142.6, 151.2, 158.6.

2-phenyl-4-carboxypyridine 2-phenyl-4-methylpyridine (6 g, 35.4 mmol) and SeO$_2$ (24 g, 216 mmol) were refluxed in pyridine (100 ml) overnight under argon. The mixture was then filtered through celite while hot. The Celite filter cake was rinsed with pyridine (3×50 ml) and the resulting filtrate evaporated to dryness. The solid thus obtained was triturated in water (200 ml) and filtered off. The resulting brown solid was suspended in a mixture of water (150 ml) and MeOH (200 ml) and made basic by addition of an aqueous NaOH solution. The mixture was then filtered over Celite to removed some insoluble materials. The filtrate was then acidified with concentrated HCl. MeOH was evaporated and the formed precipitate was filtered, washed with water, then small portions of $Et_2O$ (3×20 ml) and finally dried to afford 5.9 g (84%) of the titled compound as a slightly brown solid.

$^1$H-NMR (DMSO-d$^6$, 298K, 200 MHz, δ ppm) 7.50 (m, 3H), 7.78 (d, J=5.8 Hz, 1H), 8.12 (m, 2H), 8.29 (s, 1H), 8.86 (d, J=5.8 Hz, 1H).

$^{13}$C-NMR (DMSO-d$^6$, 298K, 50 Hz, δ ppm) 119.3, 121.8, 127.0, 129.3, 129.7, 138.3, 139.8, 151.0, 157.5, 166.6.

2-phenyl-4-methyl carboxypyridine L2

2-phenyl-4-carboxypyridine (3 g, 15 mmol) was refluxed overnight in MeOH (70 ml) and $H_2SO_4$ (4 ml). After evaporation of the solvent, water (100 ml) was added and the mixture was neutralized with saturated $NaHCO_3$ solution. The aqueous phase was then extracted with $CH_2Cl_2$ (2×100 ml). The combined organic fractions were washed with water (100 ml), brine (50 ml) and dried over $MgSO_4$. The crude compound was then flash chromatographed ($SiO_2$, $CH_2Cl_2$) to afford 2.3 g (72%) of the titled compound as a colourless oil.

$^1$H-NMR (CDCl$_3$, 298K, 200 MHz, δ ppm) 4.00 (s, 3H), 7.48 (m, 3H), 7.78 (d, J=5.8 Hz, 1H), 8.07 (m, 2H), 8.32 (s, 1H), 8.86 (d, J=5.8 Hz, 1H).

$^{13}$C-NMR (CDCl$_3$, 298K, 50 Hz, δ ppm) 52.7, 119.7, 121.1, 127.0, 128.8, 129.5, 138.2, 138.5, 150.4, 158.5, 165.8.

2-iodo-4-dimethylaminopyridine $BF_3.Et_2O$ (8.4 g, 59 mmol) was added drop-wise to a solution of 4-dimethylaminopyridine (6 g, 49 mmol) in dry THF (250 ml) at 0° C. The resulting mixture was stirred 1 hour at 0° C. under nitrogen. Temperature was cooled down to −78° C. and BuLi (1.6 M in hexane, 46 ml, 74 mmol) was added dropwise. The resulting mixture was stirred for 1 hour at −78° C. and a solution of $I_2$ (18.7 g, 74 mmol) in dry THF (50 ml) was added dropwise. The resulting mixture was stirred at −78° C. for 2 hours and allowed to warm to room temperature (2 hours). THF was evaporated and a saturated $Na_2S_2O_5$ solution was added. The resulting slurry was extracted with EtOAc (5×150 ml). The combined organic fractions were successively washed with saturated $Na_2S_2O_5$ (50 ml), brine (50 ml), dried over $MgSO_4$, filtered and evaporated to dryness. The resulting residue was purified by chromatography column ($SiO_2$, EtOAc/petroleum ether, 1/1) to afford 7 g (57%) of the desired compound as a colourless oil, which solidify upon standing.

$^1$H and $^{13}$C NMR are in agreement with those reported in the literature (Cuperly, D.; Gros, P.; Fort, Y. *J. Org. Chem.* 2002, 67, 238-241.)

2-phenyl-4-dimethylaminopyridine L3

A mixture of 2-iodo-4-dimethylaminopyridine (3.3 g, 13.3 mmol), phenylboronic acid (2.5 g, 20 mmol) and $K_2CO_3$ (8.3 g, 60 mmol) in toluene (60 ml) and water (10 ml) were degased with nitrogen for 15 minutes. Pd(PPh$_3$)$_4$ (800 mg, 0.66 mmol) was added and the resulting mixture was heated to 90° C. for 48 hours under nitrogen. After being cooled to room temperature, the aqueous phase was separated and extracted with EtOAc (3×100 ml). The combined organic fractions were washed with brine, dried over $MgSO_4$, filtered and evaporated to afford a brown oil. The following oil was dissolved in $Et_2O$ and extracted with 10% HCl solution (3×50 ml). The combined aqueous fractions were washed with $Et_2O$ (2×100 ml) and neutralized with concentrated NaOH solution. The resulting mixture was extracted with EtOAc (4×100 ml), the combined organic fractions were washed with brine (50 ml), dried over $MgSO_4$, filtered and evaporated to dryness. The obtained residue was then purified by column chromatography ($SiO_2$, $CH_2Cl_2$/MeOH, 97/3) to afford 1.2 g (46%) of the titled compound as a colorless oil, which solidify upon standing.

$^1$H-NMR (CDCl$_3$, 298K, 200 MHz, δ ppm) 3.08 (s, 6H), 6.49 (dd, J=2.5 and 6 Hz, 1H), 6.91 (s, 1H), 7.47 (m, 3H), 7.94 (d, J=7 Hz 2H), 8.34 (d, J=6 Hz, 1H).

$^{13}$C-NMR (CDCl$_3$, 298K, 50 Hz, δ ppm) 39.2, 103.6, 105.4, 127.0, 128.6, 132.2, 140.5, 149.5, 155.1, 157.8.

2-(2,4-difluorophenyl)-4-dimethylaminopyridine L4

A mixture of 2-iodo-4-dimethylaminopyridine (3 g, 12 mmol), 2,4-difluorophenylboronic acid (2.3 g, 14.5 mmol) and $K_2CO_3$ (6 g, 43.5 mmol) in toluene (60 ml) and water (10 ml) were degased with nitrogen for 15 minutes. Pd(PPh$_3$)$_4$ (800 mg, 0.66 mmol) was added and the resulting mixture was heated to 90° C. for 48 hours under nitrogen. After being cooled to room temperature, the aqueous phase was separated and extracted with EtOAc (3×100 ml). The combined organic fractions were washed with brine, dried over $MgSO_4$, filtered and evaporated. The crude compound was purified by column chromatography ($SiO_2$, CHCl$_3$ then CHCl$_3$/MeOH, 97/3) to afford 2.2 g (78%) of the titled compound as a slightly yellow oil, which solidify upon standing. If some impurities remains, the compound can be purified by following the acidic extraction followed by basic recovery as performed before for 2-phenyl-4-dimethylaminopyridine.

$^1$H-NMR (CDCl$_3$, 298K, 200 MHz, δ ppm) 3.05 (s, 6H), 6.49 (dd, J=2.5 and 6 Hz, 1H), 6.92 (m, 3H), 7.94 (m, 1H), 8.33 (d, J=6 Hz, 1H).

2-(3,5-difluorophenyl)-4-dimethylaminopyridine L5

A mixture of 2-iodo-4-dimethylaminopyridine (2.68 g, 10.8 mmol), 3,5-difluorophenylboronic acid (2.56 g, 16.2 mmol) and $K_2CO_3$ (6.7 g, 48.6 mmol) in toluene (60 ml) and water (10 ml) were degased with nitrogen for 15 minutes. Pd(PPh$_3$)$_4$ (800 mg, 0.66 mmol) was added and the resulting mixture was heated to 90° C. for 48 hours under nitrogen. After being cooled to room temperature, the aqueous phase was separated and extracted with EtOAc (3×100 ml). The combined organic fractions were washed with brine, dried over $MgSO_4$, filtered and evaporated to afford a brown oil. The following oil was dissolved in $Et_2O$ and extracted with 10% HCl solution (3×50 ml). The combined aqueous fractions were washed with $Et_2O$ (2×100 ml) and neutralized with concentrated NaOH solution. The resulting mixture was extracted with EtOAc (4×100 ml), the combined organic fractions were washed with brine (50 ml), dried over $MgSO_4$, filtered and evaporated to dryness. The obtained residue was then purified by column chromatography ($SiO_2$, EtOAc) to afford 1.2 g (46%) of the titled compound as a colorless oil, which solidify upon standing. The crude compound was purified by column chromatography ($SiO_2$, CHCl$_3$ then CHCl$_3$/

MeOH, 97/3) to afford 1 g (40%) of the titled compound as a colorless oil, which solidify upon standing.

$^1$H-NMR (CDCl$_3$, 298K, 200 MHz, δ ppm) 3.08 (s, 6H), 6.51 (dd, J=2.5 and 6 Hz, 1H), 6.82 (m, 2H), 7.49 (m, 2H), 8.32 (d, J=6 Hz, 1H).

2-(3-methoxyphenyl)-4-dimethylaminopyridine L6

A mixture of 2-iodo-4-dimethylaminopyridine (2.7 g, 11 mmol), 3-methoxyphenylboronic acid (2 g, 13 mmol) and K$_2$CO$_3$ (5.4 g, 39 mmol) in toluene (60 ml) and water (10 ml) were degased with nitrogen for 15 minutes. Pd(PPh$_3$)$_4$ (800 mg, 0.66 mmol) was added and the resulting mixture was heated to 90° C. for 48 hours under nitrogen. After being cooled to room temperature, the aqueous phase was separated and extracted with EtOAc (3×100 ml). The combined organic fractions were washed with brine, dried over MgSO$_4$, filtered and evaporated. The crude compound was purified by column chromatography (SiO$_2$, EtOAc) to afford 2.1 g (84%) of the titled compound as a colorless oil, which solidify upon standing. If some impurities remains, the compound can be purified by following the acidic extraction followed by basic recovery as performed before for 2-phenyl-4-dimethylaminopyridine.

$^1$H-NMR (CDCl$_3$, 298K, 200 MHz, δ ppm) 3.07 (s, 6H), 3.90 (s, 3H), 6.49 (dd, J=2.5 and 6 Hz, 1H), 6.96 (m, 2H), 7.45 (m, 3H), 8.34 (d, J=6 Hz, 1H).

$^{13}$C-NMR (CDCl$_3$, 298K, 50 Hz, δ ppm) 39.2, 55.4, 103.8, 105.5, 112.2, 114.5, 119.4, 129.4, 142.2, 149.6, 155.0, 157.7, 159.8.

2-phenyl-4-(p-dimethylaminostyryl)pyridine L7

To a mixture of 2-phenyl-4-methylpyridine hydrochloride (1 g, 4.86 mmol) and 4-dimethylaminobenzaldehyde (0.725 g, 4.86 mmol) in anhydrous DMF (30 ml) was added solid tBuOK and the resulting mixture was stirred 5 hours at room temperature under nitrogen. Water (200 ml) was then added, the resulting yellow precipitate was filtered off and successively washed with water and Et$_2$O to afford 650 mg (44%) of the titled compound as a yellow solid.

$^1$H-NMR (CDCl$_3$, 298K, 200 MHz, δ ppm) 3.02 (s, 6H), 6.74 (d, J=8.8 Hz, 2H), 6.89 (d, J=16 Hz, 1H), 7.3-7.5 (m, 7H), 7.75 (s, 1H), 8.03 (d, J=8.2 Hz, 2H), 8.61 (d, J=5.2 Hz, 1H).

$^{13}$C-NMR (CDCl$_3$, 298K, 50 Hz, δ ppm) 40.3, 112.2, 117.7, 118.8, 121.4, 124.3, 127.0, 128.3, 128.7, 128.8, 133.3, 139.7, 146.4, 149.8, 150.8, 157.8.

C⌒N$_2$Ir(μ-Cl)$_2$IrC⌒N$_2$ with C⌒N=L2

IrCl$_3$.3H$_2$O and L2 (2.5 eq.) were heated to reflux in 2-ethoxyethanol (30 ml) overnight under nitrogen. After being cooled to room temperature, the orange precipitate was filtered and washed with small portions of cold 2-ethoxyethanol. The resulting solid was then dissolved in CH$_2$Cl$_2$ and filtered to remove some black impurities. The filtrate was evaporated to dryness to afford the desired dimer as an orange solid (67%). $^1$H-NMR (CDCl$_3$, 298K, 200 MHz, δ ppm) 4.14 (s, 12H), 5.92 (d, J=7.6 Hz, 4H), 6.63 (t, J=7.6 Hz, 4H), 6.84 (t, J=7.6 Hz, 4H), 7.22 (d, J=6 Hz, 4H), 7.65 (d, J=7.6 Hz, 4H), 8.48 (s, 4H), 9.34 (d, J=6 Hz, 4H). $^{13}$C-NMR (CDCl$_3$, 298K, 50 Hz, δ ppm) 53.1, 118.0, 121.2, 122.0, 124.5, 129.9, 130.5, 137.6, 142.6, 145.2, 151.7, 164.8, 169.5.

C⌒N$_2$Ir(μ-Cl)$_2$IrC⌒N$_2$ with C⌒N=L1, L3, L4, L5, L6, L7

IrCl$_3$.3H$_2$O and 2.5 equivalents of the desired ligand were heated at 110° C. in a mixture of 2-ethoxyethanol (30 ml) and water (10 ml) overnight under nitrogen. After being cooled to room temperature, the resulting precipitate was filtered off, successively washed with methanol than Et$_2$O and finally dried to afford the desired dimer with yields in the range 40-70%.

C⌒N=L1: $^1$H-NMR (DMSO-d$^6$, 298K, 200 MHz, δ ppm) 2.56 (s, 6H), 2.61 (s, 6H), 5.70 (d, J=7.5 Hz, 1H), 6.26 (d, J=7.5 Hz, 1H), 6.77 (m, 4H), 7.29 (d, J=6 Hz, 1H), 7.42 (d, J=6 Hz, 1H), 7.72 (m, 2H), 8.01 (s, 1H), 8.11 (s, 1H), 9.33 (d, J=6 Hz, 1H), 9.61 (d, J=6 Hz, 1H).

C⌒N=L3: $^1$H-NMR (DMSO-d$^6$, 298K, 200 MHz, δ ppm) 3.18 (s, 6H), 3.20 (s, 6H), 5.90 (d, J=7.5 Hz, 1H), 6.34 (d, J=7.5 Hz, 1H), 6.75 (m, 6H), 7.19 (s, 1H), 7.27 (s, 1H), 7.70 (m, 2H), 8.89 (d, J=6 Hz, 1H), 9.27 (d, J=6 Hz, 1H).

C⌒N=L4: $^1$H-NMR (DMSO-d$^6$, 298K, 200 MHz, δ ppm) 3.16 (s, 6H), 3.19 (s, 6H), 5.35 (dd, J=2 and 8.7 Hz, 1H), 5.83 (dd, J=2 and 8.7 Hz, 1H), 6.70-7.00 (m, 4H), 7.37 (m, 2H), 8.86 (d, J=7 Hz, 1H), 9.21 (d, J=7 Hz, 1H).

C⌒N=L5: $^1$H-NMR (DMSO-d$^6$, 298K, 200 MHz, δ ppm) 3.14 (s, 6H), 3.17 (s, 6H), 6.30-6.80 (m, 4H), 7.20 (d, J=2.5 Hz, 1H), 7.28 (d, J=2.5 Hz, 1H), 7.69 (m, 2H), 8.90 (d, J=7 Hz, 1H), 9.21 (d, J=7 Hz, 1H).

C⌒N=L6: $^1$H-NMR (DMSO-d$^6$, 298K, 200 MHz, δ ppm) 3.14 (s, 6H), 3.17 (s, 6H), 3.64 (s, 3H), 3.65 (s, 3H), 5.71 (d, J=8.3 Hz, 1H), 6.15 (d, J=8.3 Hz, 1H), 6.40 (m, 2H), 6.65 (m, 1H), 6.79 (m, 1H), 7.29 (m, 4H), 8.76 (d, J=7 Hz, 1H), 9.25 (d, J=7 Hz, 1H).

A Representative Synthetic Protocol for Complex 1-1: TBA[Ir(L)$_2$(CN)$_2$]

The dimeric iridium (III) complex [Ir(L)$_2$(Cl)]$_2$ (1 equivalent) was dissolved in 30 ml of dichloromethane solvent under nitrogen. To this solution was added tetrabutylammonium cyanide (4-20 equivalents) ligand. The reaction mixture was refluxed with stirring for 1-15 hours. Then, to the solution was added 1:1 solvent mixture of diethyl ether and low-boiling petroleum ether (60 ml). The precipitated solid was collected and recrystallized from methanol and low-boiling petroleum ether. Yield 87%.

Analytical, electrochemical, and spectroscopic data are consistent with the TBA[Ir(L)$_2$(CN)$_2$]

A Representative Synthetic Procedure for Complex 2-1: TBA[Ir(ppy)$_2$(NCS)$_2$].

Using the same conditions as for 1-1 complex, starting from the dimeric iridium (III) complex and tetrabutylammonium thiocyanate the compound 2-1 was obtained as a yellow powder (Yield 72%).

Analytical, electrochemical, and spectroscopic data are consistent with the TBA[Ir(ppy)$_2$(NCS)$_2$].

A Representative Synthetic Procedure for Complex 3-1: [Ir(L)$_2$(L')]PF$_6$

Using the same conditions as for 1-1 complex, starting from the dimeric iridium (III) complex and 4,4'-dimethylamino-2,2'-bipyridine (L') the compound 3-1 was obtained as a yellow powder (Yield 50%).

Analytical, electrochemical, and spectroscopic data are consistent with the [Ir(L)$_2$(L')]PF$_6$ A Representative Synthetic Procedure for Complex 4-1: [Ir(L)$_2$(L')]PF$_6$ Using the same conditions as for 1-1 complex, starting from the dimeric iridium (III) complex and 4,4'-dialkyloxy-2,2'-bipyridine the compound 4-1 was obtained as a yellow powder (Yield 70%).

Analytical, electrochemical, and spectroscopic data are consistent with the [Ir(L)$_2$(L')]PF$_6$ A Representative Synthetic Procedure for Complex 5-1: TBA[Ir(L)$_2$(CN)$_2$]

Using the same conditions as for 1-1 complex, starting from the dimeric iridium (III) complex and tetrabutylammonium cyanide the compound 5-1 was obtained (Yield 72%).

Analytical, electrochemical, and spectroscopic data are consistent with the TBA[Ir(L)$_2$(CN)$_2$].

A Representative Synthetic Procedure for Complex 6-1: TBA [Ir(ppy)$_2$(NCS)$_2$].

Using the same conditions as for 1-1 complex, starting from the dimeric iridium (III) complex and tetrabutylammonium thiocyanate the compound 6-1 was obtained as a yellow powder (Yield 75%).

Analytical, electrochemical, and spectroscopic data are consistent with the TBA[Ir(ppy)$_2$(NCS)$_2$].

A Representative Synthetic Procedure for Complex 7-1: [Ir(L)$_2$(L')]PF$_6$

Using the same conditions as for 1-1 complex, starting from the dimeric iridium (III) complex and 4,4'-dialkylamino-2,2'-bipyridine the compound 7-1 was obtained (Yield 55%).

Analytical, electrochemical, and spectroscopic data are consistent with the [Ir(L)$_2$(L')]PF$_6$ A Representative Synthetic Procedure for Complex 8-1: [Ir(L)$_2$(L')]PF$_6$ Using the same conditions as for 1-1 complex, starting from the dimeric iridium (III) complex and 4,4'-dialkyloxy-2,2'-bipyridine the compound 8-1 was obtained (Yield 60%).

Analytical, electrochemical, and spectroscopic data are consistent with the [Ir(L)$_2$(L')]PF$_6$ A Representative Synthetic Procedure for Complex 9-1: [Ir(L)$_2$(acac)]

The dimeric iridium (III) complex [Ir(L)$_2$(Cl)]$_2$ (1 equivalent) was dissolved in 30 ml of dichloromethane solvent under nitrogen. To this solution was added acetyl acetone (2-3 equivalents), which was dissolved in 0.5 ml of ethanol. The reaction mixture was refluxed with stirring for 1-15 hours. Then, tetrabutyl ammonium hydroxide (2 equivalent) was introduced into the reaction mixture and was refluxed for 5 hours. After which the solution was evaporated to dryness and the resulting solid was collected on a sintered glass crucible, washed thoroughly with ethanol. The yield of the dried product is 90%.

Analytical, electrochemical, and spectroscopic data are consistent with the [Ir(L)$_2$(acac)]

A Representative Synthetic Procedure for complex 10-1: [Ir(L)$_3$]

The dimeric iridium (III) complex [Ir(L)$_2$(Cl)]$_2$ (1 equivalent) was dissolved in 30 ml of methoxyethanol solvent under nitrogen. To this solution was added L (2-3 equivalents), and then the reaction mixture was refluxed with stirring for 1-2 hours. Then, tetrabutyl ammonium hydroxide (2 equivalent) was introduced into the reaction mixture and was refluxed for 10-25 hours. After which the solution was evaporated to dryness and the resulting solid was collected on a sintered glass crucible, washed thoroughly with ethanol. The yield of the dried product is 90%.

Analytical, electrochemical, and spectroscopic data are consistent with the [Ir(L)$_3$]

A Representative Synthetic Procedure for Complex 11-1: [Ir(L)$_2$(acac)]

The dimeric iridium (III) complex [Ir(L)$_2$(Cl)]$_2$ (1 equivalent) was dissolved in 30 ml of dichloromethane solvent under nitrogen. To this solution was added acetyl acetone (2-3 equivalents), which was dissolved in 0.5 ml of ethanol. The reaction mixture was refluxed with stirring for 1-15 hours. Then, tetrabutyl ammonium hydroxide (2 equivalent) was introduced into the reaction mixture and was refluxed for 5 hours. After which the solution was evaporated to dryness and the resulting solid was collected on a sintered glass crucible, washed thoroughly with ethanol. The yield of the dried product is 90%.

Analytical, electrochemical, and spectroscopic data are consistent with the [Ir(L)$_2$(acac)]

A Representative Synthetic Procedure for Complex 12-1: [Ir(L)$_3$]

The dimeric iridium (III) complex [Ir(L)$_2$(Cl)]$_2$ (1 equivalent) was dissolved in 30 ml of methoxyethanol solvent under nitrogen. To this solution was added L (2-3 equivalents), and then the reaction mixture was refluxed with stirring for 1-2 hours. Then, tetrabutyl ammonium hydroxide (2 equivalent) was introduced into the reaction mixture and was refluxed for 10-25 hours. After which the solution was evaporated to dryness and the resulting solid was collected on a sintered glass crucible, washed thoroughly with ethanol. The yield of the dried product is 90%.

Analytical, electrochemical, and spectroscopic data are consistent with the [Ir(L)$_3$]

A Representative Synthetic Procedure for Complex 13-1: [Ir(L)$_2$(L')]

Using the same conditions as for 1-1 complex, starting from the dimeric iridium (III) complex and L' ligand the compound 13-1 was obtained as a yellow powder (Yield 70%).

Analytical, electrochemical, and spectroscopic data are consistent with the [Ir(L)$_2$(L')]

A Representative Synthetic Procedure for Complex 14-1: [Ir(L)$_2$(acac)]

The dimeric iridium (III) complex [Ir(L)$_2$(Cl)]$_2$ (1 equivalent) was dissolved in 30 ml of dichloromethane solvent under nitrogen. To this solution was added acetyl acetone (2-3 equivalents), which was dissolved in 0.5 ml of ethanol. The reaction mixture was refluxed with stirring for 1-15 hours. Then, tetrabutyl ammonium hydroxide (2 equivalent) was introduced into the reaction mixture and was refluxed for 5 hours. After which the solution was evaporated to dryness and the resulting solid was collected on a sintered glass crucible, washed thoroughly with ethanol. The yield of the dried product is 90%.

Analytical, electrochemical, and spectroscopic data are consistent with the [Ir(L)$_2$(acac)]

REFERENCES

1. Q. Pei, G. Yu, Y. Zhang, Y. Yang and A. J. Heeger, Science 269, 1086 (1995).
2. B. W. D'Andrade, M. E. Thompson, and S. R. Forrest, Advanced Materials 14, 147 (2002).
3. V. V. Grushin, N. Herron, D. D. LeCloux, W. J. Marshall, V. A. Petrov and Y. Wang, Chemical Communications 2001, 1494 (2001).
4. P. Coppo, E. A. Plummer, and L. De Cola, Chemical Communications 2004, 1774 (2004).
5. Brian W. D'Andrade, Marc A. Baldo, Chihaya Adachi, Jason Brooks, Mark E. Thompson, and Stephen R. Forrest "High-efficiency yellow double-doped organic light-emitting devices based on phosphor-sensitized fluorescence" Appl. Phys. Lett., 79, 1045 (2001).
6. Jason D. Slinker, Alon A. Gorodetsky, Michael S. Lowry, Jingjing Wang, Sara Parker, Richard Rohl, Stefan Bernhard, and George G. Malliaras "Efficient Yellow Electroluminescence from a Single Layer of a Cyclometalated Iridium Complex", J. Am. Chem. Soc., 126, 2763 (2004).

The invention claimed is:

1. A metal complex having at least one metal atom selected from the group consisting of Ir, Os, Ru, Pd, Pt, Re and Zn, said metal complex comprising at least one ligand that is a 2-phenylpyridine ligand (I), comprising a phenyl ring (A) and a pyridine ring (B),

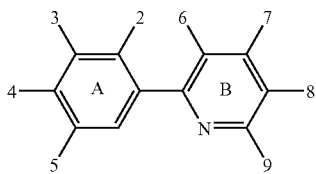
(I)

where the integers 2 to 9 denote positions in which substitutions can be made, and wherein said pyridine ring (B) is substituted by 4-dimethylaminostyryl.

2. The metal complex of claim 1, wherein said at least one metal atom includes Ir.

3. The metal complex of claim 1, wherein said phenyl ring (A) is non-substituted or substituted in one of the following ways:
position 2=fluoro and position 4=fluoro; or
position 3=fluoro and position 5=fluoro; or
position 3=OR
R being the same or different at each occurrence and is H, alkyl, aryl, or adjacent R groups can join together to form a 5- or 6-membered ring.

4. The metal complex of claim 3, wherein said pyridine ring (B) is substituted at position 7 with 4-dimethylaminostyryl or with a compound of the following formula (II):

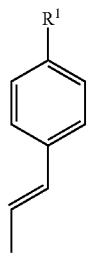
(II)

wherein $R^1$ is 4-dimethylaminostyryl.

5. The metal complex of claim 3, wherein R is $CH_3$.

6. The metal complex of claim 3, wherein said metal complex comprises at least one ligand L2 that includes at least one compound of the following formula (III):

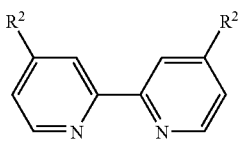
(III)

wherein $R^2$ is selected from $NR_2$ or OR;
R being the same or different at each occurrence and is H, alkyl, aryl, or adjacent R groups can join together to form a 5- or 6-membered ring.

7. The metal complex of claim 6, wherein the metal complex is anionic or cationic.

8. The metal complex of claim 7, wherein said phenyl ring (A) is non-substituted and wherein $R^2$ of the ligand L2 is $NR_2$.

9. The metal complex of claim 7, wherein said phenyl ring (A) is substituted by fluoro in positions 2 and 4 and wherein $R^2$ of the ligand L2 is $NR_2$.

10. The metal complex of claim 7, wherein the metal complex comprises $(R^3)_4N^+$, $NH_4^+$, $(R^3)_4P^+$, $Li^+$, $Na^+$, $K^+$, $Rb^+$, $Cs^+$, $Ag^+$, $Cu^+$, $PF_6^-$, $F^-$, $Cl^-$, $I^-$, $Br^-$, $ClO_4^-$, $BF_4^-$, $CF_3SO_3^-$, $(R^3)_4B^-$, or mixtures thereof, wherein $R^3$ is an alkyl or aryl group.

11. The metal complex of claim 10, wherein $R^3$ is butyl.

12. A method for manufacturing a light-emitting device comprising arranging an electroluminescent material between at least two electrodes, wherein said electroluminescent material comprises a metal complex according to claim 1.

* * * * *